(12) United States Patent
Long et al.

(10) Patent No.: US 7,489,252 B2
(45) Date of Patent: *Feb. 10, 2009

(54) WETNESS MONITORING SYSTEMS WITH STATUS NOTIFICATION SYSTEM

(75) Inventors: Andrew Mark Long, Appleton, WI (US); Christopher Peter Olson, Neenah, WI (US); Thomas Michael Ales, III, Neenah, WI (US); Shirlee Ann Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 328 days.

This patent is subject to a terminal disclaimer.

(21) Appl. No.: 11/412,351

(22) Filed: Apr. 26, 2006

(65) Prior Publication Data

US 2007/0252710 A1 Nov. 1, 2007

(51) Int. Cl.
G08B 21/00 (2006.01)
(52) U.S. Cl. .................. 340/604; 340/573.5
(58) Field of Classification Search ............. 340/604, 340/605, 573.5; 604/361
See application file for complete search history.

(56) References Cited

U.S. PATENT DOCUMENTS

| | | | | |
|---|---|---|---|---|
| 3,778,570 A * | 12/1973 | Shuman | ............... | 340/604 |
| 4,100,324 A | 7/1978 | Anderson et al. | | |
| 4,269,206 A | 5/1981 | Boyd | | |
| 4,704,116 A | 11/1987 | Enloe | | |
| 4,940,464 A | 7/1990 | Van Gompel et al. | | |
| 5,043,704 A * | 8/1991 | Blakeney | ............... | 340/573.5 |
| 5,114,781 A | 5/1992 | Morman | | |
| 5,116,662 A | 5/1992 | Morman | | |
| 5,266,928 A | 11/1993 | Johnson | | |
| 5,284,703 A | 2/1994 | Everhart et al. | | |
| 5,350,624 A | 9/1994 | Georger et al. | | |
| 5,486,166 A | 1/1996 | Bishop et al. | | |
| 5,490,846 A | 2/1996 | Ellis et al. | | |
| 5,537,095 A * | 7/1996 | Dick et al. | ............... | 340/573.5 |
| 5,645,542 A | 7/1997 | Anjur et al. | | |
| 5,766,389 A | 6/1998 | Brandon et al. | | |
| 5,820,973 A | 10/1998 | Dodge et al. | | |
| 5,883,028 A | 3/1999 | Morman et al. | | |
| 5,964,743 A | 10/1999 | Abuto et al. | | |
| 6,097,297 A * | 8/2000 | Fard | ............... | 340/604 |
| 6,163,262 A | 12/2000 | Wu | | |
| 6,231,557 B1 | 5/2001 | Krautkramer et al. | | |
| 6,246,330 B1 * | 6/2001 | Nielsen | ............... | 340/604 |
| 6,362,389 B1 | 3/2002 | McDowall et al. | | |

(Continued)

FOREIGN PATENT DOCUMENTS

CA 2 361 132 A1 5/2002

(Continued)

*Primary Examiner*—John A Tweel, Jr.
(74) *Attorney, Agent, or Firm*—David J. Arteman

(57) ABSTRACT

A monitor, for use with an absorbent article having a wetness sensor, includes a microprocessor and a current source, the microprocessor forms part of a wetness monitoring circuit and part of a continuity monitoring circuit.

A method of providing a system for monitoring an absorbent article with a wetness sensor includes programming a microprocessor to (1) provide notification when the monitor is not electrically connected with the wetness sensor, (2) provide notification when the monitor is electrically connected with the wetness sensor, and (3) provide notification when the absorbent article is wet.

17 Claims, 19 Drawing Sheets

U.S. PATENT DOCUMENTS

| | | |
|---|---|---|
| 6,552,245 B1 | 4/2003 | Roessler et al. |
| 6,641,134 B1 | 11/2003 | Dobbertin et al. |
| 6,645,190 B1 | 11/2003 | Olson et al. |
| 7,053,781 B1 | 5/2006 | Haire et al. |
| 2002/0070868 A1 | 6/2002 | Jeutter et al. |
| 2003/0011479 A1 | 1/2003 | Bluteau |
| 2004/0152208 A1 | 8/2004 | Hutchinson |
| 2004/0207530 A1 | 10/2004 | Nielsen |
| 2005/0137542 A1 | 6/2005 | Underhill et al. |
| 2006/0244614 A1 | 11/2006 | Long |
| 2007/0049881 A1 | 3/2007 | Ales et al. |
| 2007/0049882 A1 | 3/2007 | Long et al. |
| 2007/0049883 A1 | 3/2007 | Ales et al. |
| 2007/0049884 A1 | 3/2007 | Long et al. |
| 2007/0142796 A1 | 6/2007 | Mosbacher et al. |
| 2007/0142797 A1 | 6/2007 | Long et al. |
| 2007/0142799 A1 | 6/2007 | Ales et al. |
| 2007/0252711 A1 | 11/2007 | Long et al. |

FOREIGN PATENT DOCUMENTS

| | | |
|---|---|---|
| DE | 299 05 531 U1 | 9/1999 |
| WO | WO 00/37009 A2 | 6/2000 |
| WO | WO 03/051254 A2 | 6/2003 |

* cited by examiner

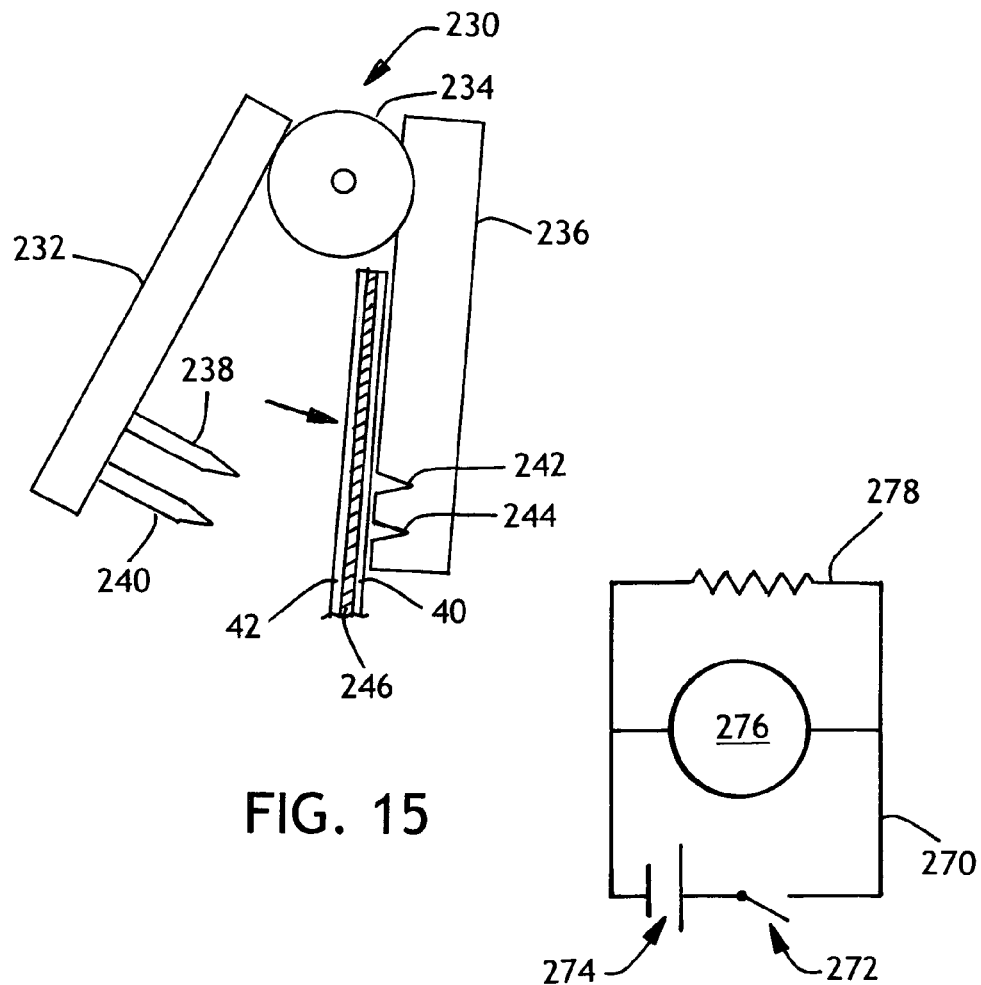
FIG. 15
FIG. 17
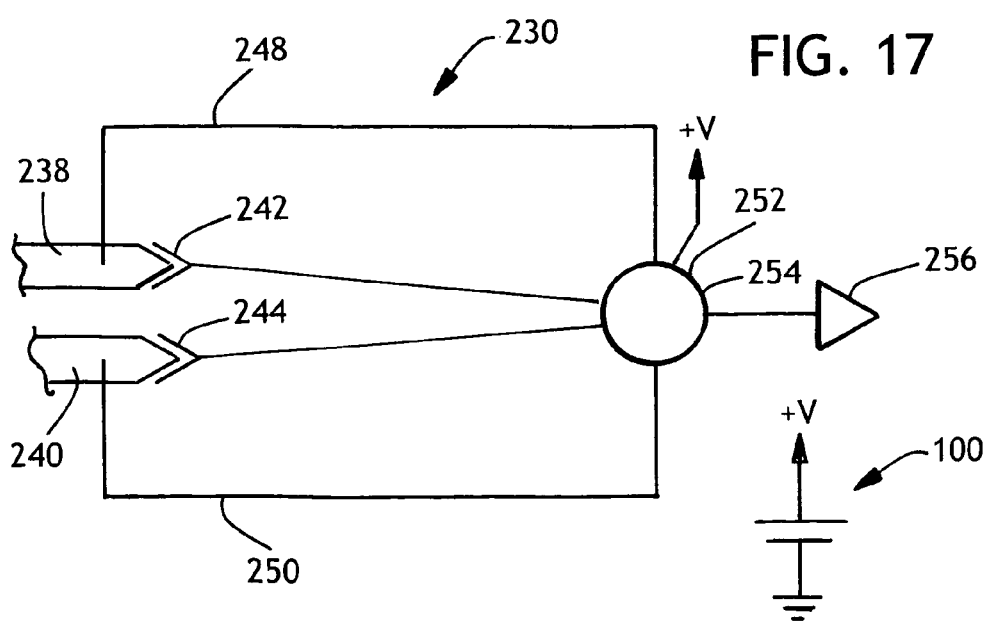
FIG. 16

WETNESS MONITORING SYSTEMS WITH STATUS NOTIFICATION SYSTEM

BACKGROUND OF THE INVENTION

The present invention relates generally to a monitoring system for detecting the presence of an insult in an absorbent article while it is being worn by a wearer. More particularly, the present invention relates to wetness monitors and wetness monitoring systems that provide notification to a caregiver that the system is operational and/or securely attached.

Disposable absorbent articles find widespread use as personal care products such as diapers, children's toilet training pants and other infant and child care products, adult incontinence garments and other adult care products, sanitary napkins and other feminine care products, and the like, as well as surgical bandages and sponges and medical garments. These articles absorb and contain body waste and are intended to be discarded after a limited period of use; i.e., the articles are not intended to be laundered or otherwise restored for reuse. Conventional disposable absorbent articles comprise an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass through for absorption by the absorbent body.

Disposable absorbent training pants, in particular, are useful in toilet training children. Typically, these disposable undergarments are similar to washable, cloth underwear in the manner in which they are put on and worn, yet provide an absorbent function similar to diapers to maintain skin health. Training pants provide a child undergoing toilet training with an undergarment that eases the transition from diapers to washable, cloth underwear as they become more confident in their ability to use the toilet independently.

Monitoring of a toilet-training child by a caregiver can be helpful in that when urination occurs it can be discussed by the child and caregiver to enhance and improve the learning experience. Therefore, it is beneficial to provide the caregiver with immediate notification and/or verification that urination has occurred so that it may be discussed with the child while the event is still fresh in the child's mind.

Likewise, caregivers tending to the hygienic needs of care recipients can benefit by monitoring the occurrences of urination in the care recipients so that the absorbent articles may be changed when necessary, but repeated inspection is not required. Therefore, it is beneficial to provide the caregiver with immediate notification that urination has occurred so that appropriate action may be taken.

One way of monitoring urination is by using a system that detects a change in an electrical property of the undergarment which electrical property is a function of the wetness of the undergarment. For example, the electrical property may be resistance, conductance, impedance, capacitance or any other parameter which varies as the wetness of the undergarment varies. For example, a pair of spaced apart parallel conductors may be situated within the absorbent material of the undergarment. These conductors are in electrical contact with the absorbent material of the undergarment and are connected to a monitor to complete a wetness circuit including a power source, such as a battery. For example; the circuit may comprise a voltage divider for detecting resistance between the conductors. The output of the circuit is an analog output voltage that corresponds to a resistance value. When the undergarment is dry, the resistance between the conductors is extremely high and relatively infinite, appearing as an open circuit. When the undergarment is wet, more particularly when the absorbent material of the undergarment between the conductors becomes wet, the resistance of the undergarment at that area drops to a relatively lower value because urine acts as a conductor.

Accordingly, in a conventional system the resistance between the conductors is monitored and compared to a predetermined and fixed threshold resistance value. If a resistance value is less than the threshold resistance value, then the wetness circuit sends a signal to an indicator, which notifies the caregiver and/or the wearer that the wearer has urinated.

Despite their usefulness, these conventional devices may be prone to improper alignment, improper attachment or other wearer errors that prevent the devices from reliably functioning as designed. Accordingly, there is a need for wetness monitoring systems that provide notification as to proper alignment and attachment.

SUMMARY OF THE INVENTION

In response to the discussed need, the present invention provides a monitor for use with an absorbent article having a wetness sensor. The monitor includes a microprocessor and a current source. The microprocessor forms part of a wetness monitoring circuit and part of a continuity monitoring circuit.

The microprocessor may further form part of a first continuity monitoring circuit and part of a second continuity monitoring circuit. The microprocessor may include programming instructions to activate an indicator when both the first continuity monitoring circuit and the second continuity monitoring circuit are complete.

The monitor may further include a first contact, a second contact, a third contact and a fourth contact. The first continuity monitoring circuit may include the first contact and the second contact. The first contact and the second contact may be adapted to electrically connect the microprocessor with a first conductor associated with an absorbent article, wherein the first conductor forms part of a wetness sensor. The second continuity monitoring circuit may include the third contact and the fourth contact. The third contact and the fourth contact may be adapted to electrically connect the microprocessor with a second conductor associated with the absorbent article, wherein the second conductor also forms part of the wetness sensor.

In some embodiments, the wetness monitoring circuit may include at least one of the first contact or the second contact and may include at least one of the third contact or the fourth contact.

In some embodiments, the first, second, third and fourth contacts may be adapted to penetrate through a bodyside liner or an outer cover of the absorbent article to electrically connect with the first and second conductors.

In some embodiments, the first, second, third and fourth contacts may be adapted to snap onto the absorbent article to electrically connect with the first and second conductors.

In various embodiments, the monitor may include a microprocessor that further forms part of an attachment monitoring circuit. The microprocessor may be adapted to provide an indication when the attachment monitoring circuit is complete.

In various embodiments, the monitor may define an open condition and a closed condition. In various embodiments, the monitor may include a hinge and a housing, wherein the attachment circuit includes a first contact associated with the hinge and a second contact associated with the housing. The first contact may be electrically connected with the second contact when the monitor is in the closed condition and the first contact may be electrically disconnected with the second contact when the monitor is in the open condition.

In various embodiments, the monitor may be part of a wetness monitoring kit. The kit may include a monitor and an absorbent article having a wetness sensor. The monitor and the article may be adapted to physically connect together. The monitor and the wetness sensor may be adapted to electrically connect together. In some embodiments, the wetness sensor may include a first conductor and a second conductor extending generally in a longitudinal direction and spaced apart in a lateral direction by a distance, D. The monitor may include a first contact, a second contact, a third contact and a fourth contact. The first contact and the second contact may be generally aligned in the longitudinal direction and the third contact and the fourth contact may be generally aligned in the longitudinal direction. The first contact and the second contact may be spaced apart from the third contact and the fourth contact by a distance of about D as measured in the lateral direction.

In some embodiments, the wetness monitoring kit may further include instructions. The instruction may direct a wearer or caregiver to attach the monitor to the absorbent article such that the first contact and the second contact electrically connect with the first conductor. The instruction may also direct a wearer or caregiver to attach the monitor to the absorbent article such that the third contact and the fourth contact electrically connect with the second conductor. The instructions may further direct a wearer or caregiver to receive a notification when the monitor has continuity with the sensor. The instructions may further direct the wearer or caregiver to reposition the monitor if no notification is received. The instructions may further direct the wearer or caregiver to reposition the monitor if a notification is received indicating that continuity is broken.

In another embodiment, the present invention provides a method of providing a system for monitoring an absorbent article with a wetness sensor. The wetness sensor includes a first conductor and a second conductor. The method includes providing a monitor having a first contact, a second contact, a microprocessor and a current source. The first contact may be adapted to electrically connect with the first conductor of the wetness sensor and the second contact may be adapted to electrically connect with the second conductor of the wetness sensor. The method further includes electrically connecting the first contact and the second contact with the microprocessor to form part of a monitoring circuit. The method further includes programming the microprocessor to measure an electrical property of the monitoring circuit, programming the microprocessor to provide a first indication when the electrical property is above a first value, programming the microprocessor to provide a second indication when the electrical property is below the first value and above a second value, and programming the microprocessor to provide a third indication when the electrical property is below the second value.

In various embodiments, the first value may be about 10 MΩ (mega ohms) and the second value may be about 1 MΩ. In various embodiments, the first indication may provide notification that the monitor is not electrically connected with the wetness sensor of the absorbent article. The second indication may provide notification that the monitor is electrically connected with the wetness sensor. The third indication may provide notification that the absorbent article is wet.

In another embodiment, the present invention provides a method of providing a monitor for use with a wetness sensor in an absorbent article, wherein the wetness sensor includes a first conductor and a second conductor. The method includes providing a monitor housing having a microprocessor associated therewith, positioning a first contact and a second contact on the monitor housing to align with the first conductor of the wetness sensor and positioning a third contact and a fourth contact on the monitor housing to align with the second conductor of the wetness sensor. The method further includes electrically connecting the first contact and the second contact with the microprocessor to define part of a first continuity monitoring circuit, electrically connecting the third contact and the fourth contact with the microprocessor to define part of a second continuity monitoring circuit, and electrically connecting at least one of the first or second contacts and at least one of the third or fourth contacts with the microprocessor to define part of a wetness monitoring circuit. The method further includes programming the microprocessor to measure an electrical property of the first continuity monitoring circuit, programming the microprocessor to measure an electrical property of the second continuity monitoring circuit, programming the microprocessor to provide a first indication when both the first continuity monitoring circuit and second continuity monitoring circuit are complete, programming the microprocessor to measure an electrical property of the wetness monitoring circuit, and programming the microprocessor to provide a second indication when an insult is detected in the wetness monitoring circuit.

In some embodiments, the monitor housing may include a pair of attachment legs pivotally attached by a hinge to a main housing wherein the hinge includes a fifth contact and one of the attachment legs or the main housing includes a sixth contact. The method may further include electrically connecting the fifth contact and the sixth contact with the microprocessor to define an attachment monitoring circuit, programming the microprocessor to measure an electrical property of the attachment monitoring circuit, and programming the microprocessor to provide a third indication when the fifth contact electrically connects with the sixth contact to complete the attachment monitoring circuit.

In some embodiments, the method may further include programming the microprocessor to provide a fourth indication when at least one of the first continuity monitoring circuit or the second continuity monitoring circuits are opened after both circuits have been closed.

In some embodiments, the monitor housing may include a pair of attachment legs pivotally attached by a hinge to a main housing and the method may further include positioning at least one of the first, second, third or fourth contacts on the attachment legs, positioning a receptacle on the main housing to align with the at least one contact when the monitor is in a closed condition, electrically connecting the at least one contact and the receptacle with the microprocessor to define an attachment monitoring circuit, and programming the microprocessor to provide a third indication when the at least one contact electrically connects with the receptacle to complete the attachment monitoring circuit.

BRIEF DESCRIPTION OF THE DRAWINGS

FIG. 15 is a side view of an exemplary monitor;

FIG. 16 schematically illustrates a first and a second attachment circuit of the monitor of FIG. 15;

FIG. 17 schematically illustrates an exemplary power management circuit;

Corresponding reference characters indicate corresponding parts throughout the drawings.

DETAILED DESCRIPTION OF THE DRAWINGS

The monitors and absorbent articles of the present invention are adapted to form all or part of a monitoring system for detecting the presence of an insult (e.g., urine, feces, menstrual fluid, blood, and the like). In general, one or more sensors are used to detect the insult. The system monitors an electrical property of the sensor (e.g., resistance, conductivity, and the like) and based on the changes in the electrical property, determines whether the absorbent article has been insulted. After detecting the presence of the insult, a caregiver and/or a wearer of the absorbent article is signaled as to the presence of the insult. The signal may be, for example, an auditory signal, such as a song; a tactile signal, such as temperature change, pressure, and/or vibration; and/or a visual signal, such as a blinking light, a visual message, or the like. It will be understood that other signals are within the scope of the present disclosure. It is also understood that the monitoring system may comprise a device for sending a wireless signal to a remote auditory, visual, tactile or other sensory alarm.

Figure 1:
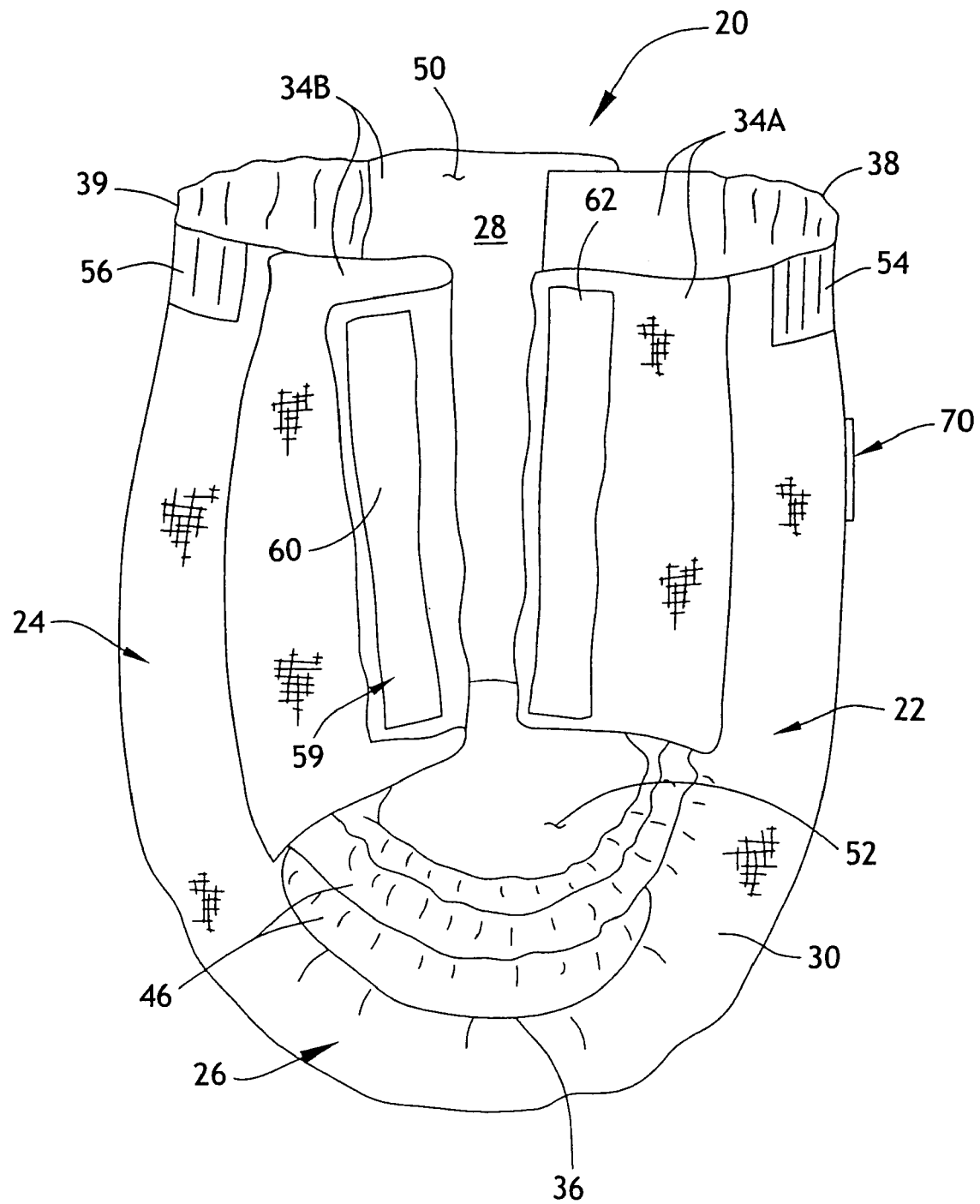
FIG. 1 is a side perspective view of an exemplary article adapted to function as part of a wetness monitoring system.

Referring now to the drawings and in particular to FIG. 1, an exemplary absorbent article of the present invention is representatively illustrated therein in the form of children's toilet training pants and is indicated in its entirety by the reference numeral 20. The absorbent article 20 may or may not be disposable, which refers to articles that are intended to be discarded-after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like, without departing from the scope of the present invention.

By way of illustration only, various materials and methods for constructing training pants are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

Figure 4:
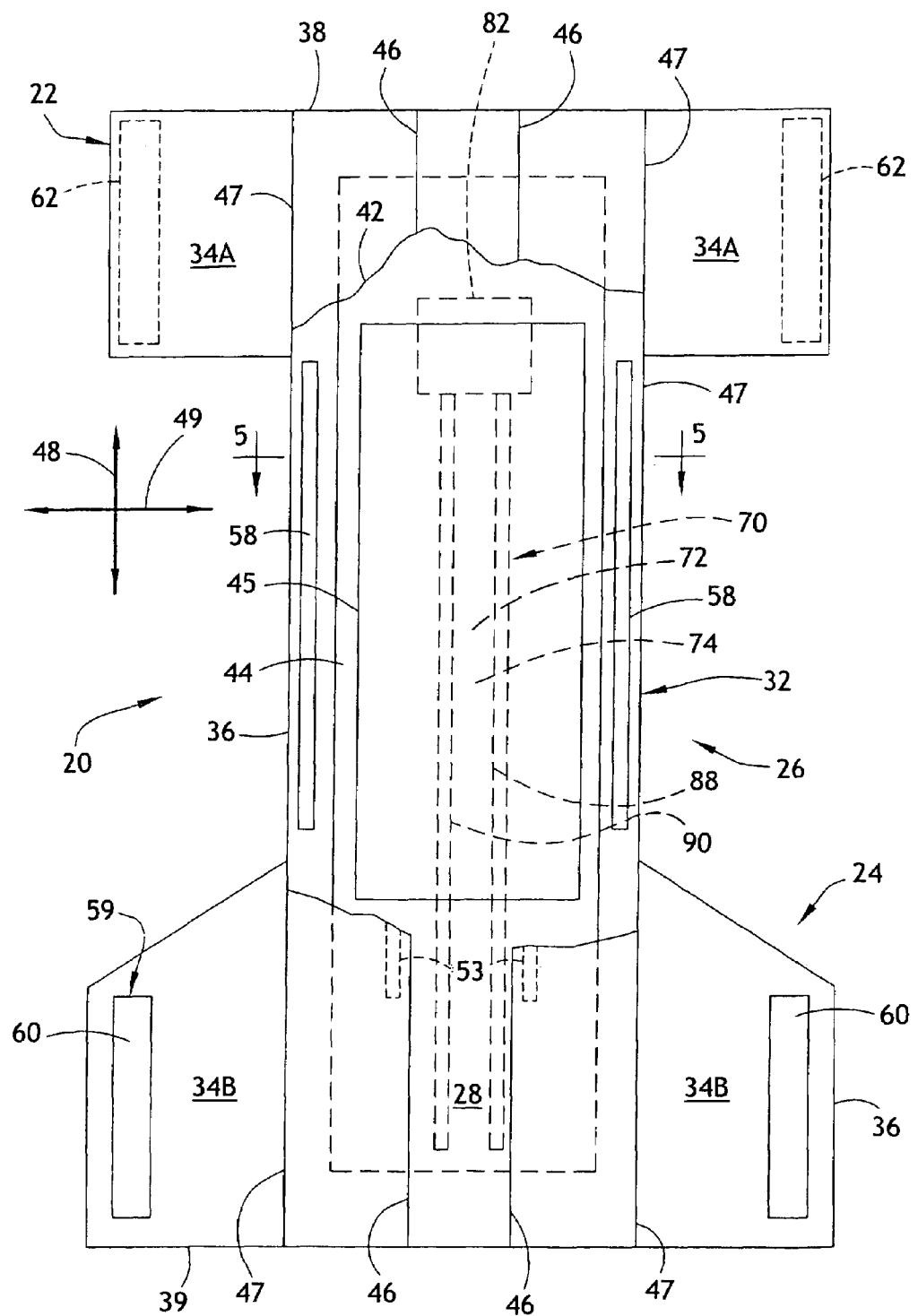
FIG. 4 is a top plan view of the training pants of FIG. 1 with the pants in an unfastened, unfolded and laid flat condition, with portions cut away to show underlying features.

The pair of training pants 20 is illustrated in FIG. 1 in a partially fastened condition. The pants 20 define a longitudinal direction 48 of the pants and a lateral direction 49 thereof perpendicular to the longitudinal direction as shown in FIG. 4. The pants 20 further define a pair of longitudinal end regions, otherwise referred to herein as a front waist region, generally indicated at 22, and a back waist region, generally indicated at 24, and a center region, otherwise referred to herein as a crotch region, generally indicated at 26, extending longitudinally between and interconnecting the front and back waist regions 22, 24. The front and back waist regions 22, 24 comprise those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 that faces toward the wearer when the pants are being worn, and an outer surface 30 opposite the inner surface. With additional reference to FIG. 4, the pair of training pants 20 has a pair of laterally opposite side edges 36 and a pair of longitudinally opposite waist edges. (broadly, longitudinal ends), respectively designated front waist edge 38 and back waist edge 39.

In the embodiment of FIGS. 1-4, the training pants 20 comprise a generally rectangular central absorbent assembly, generally indicated at 32, and side panels 34A, 34B formed separately from and secured to the central absorbent assembly. The side panels 34A, 34B are permanently bonded along seams to the central absorbent assembly 32 in the respective front and back waist regions 22 and 24 of the pants 20. More particularly, the front side panels 34A can be permanently bonded to and extend transversely outward beyond side margins 47 of the absorbent assembly 32 at the front waist region 22, and the back side panels 34B can be permanently bonded to and extend transversely outward beyond the side margins of the absorbent assembly at the back waist region 24. The side panels 34A and 34B may be bonded to the absorbent assembly 32 using attachment means known to those skilled in the art such as adhesive, thermal or ultrasonic bonding.

The front and back side panels 34A and 34B, upon wearing of the pants 20, thus comprise the portions of the training pants 20 which are positioned on the hips of the wearer. The front and back side panels 34A and 34B can be permanently bonded together to form the three-dimensional configuration of the pants 20, or be releasably connected with one another such as by a fastening system 59 of the illustrated aspects. As is known in the art, the side panels 34A, 34B may comprise elastic material or stretchable but inelastic materials.

Figure 2:
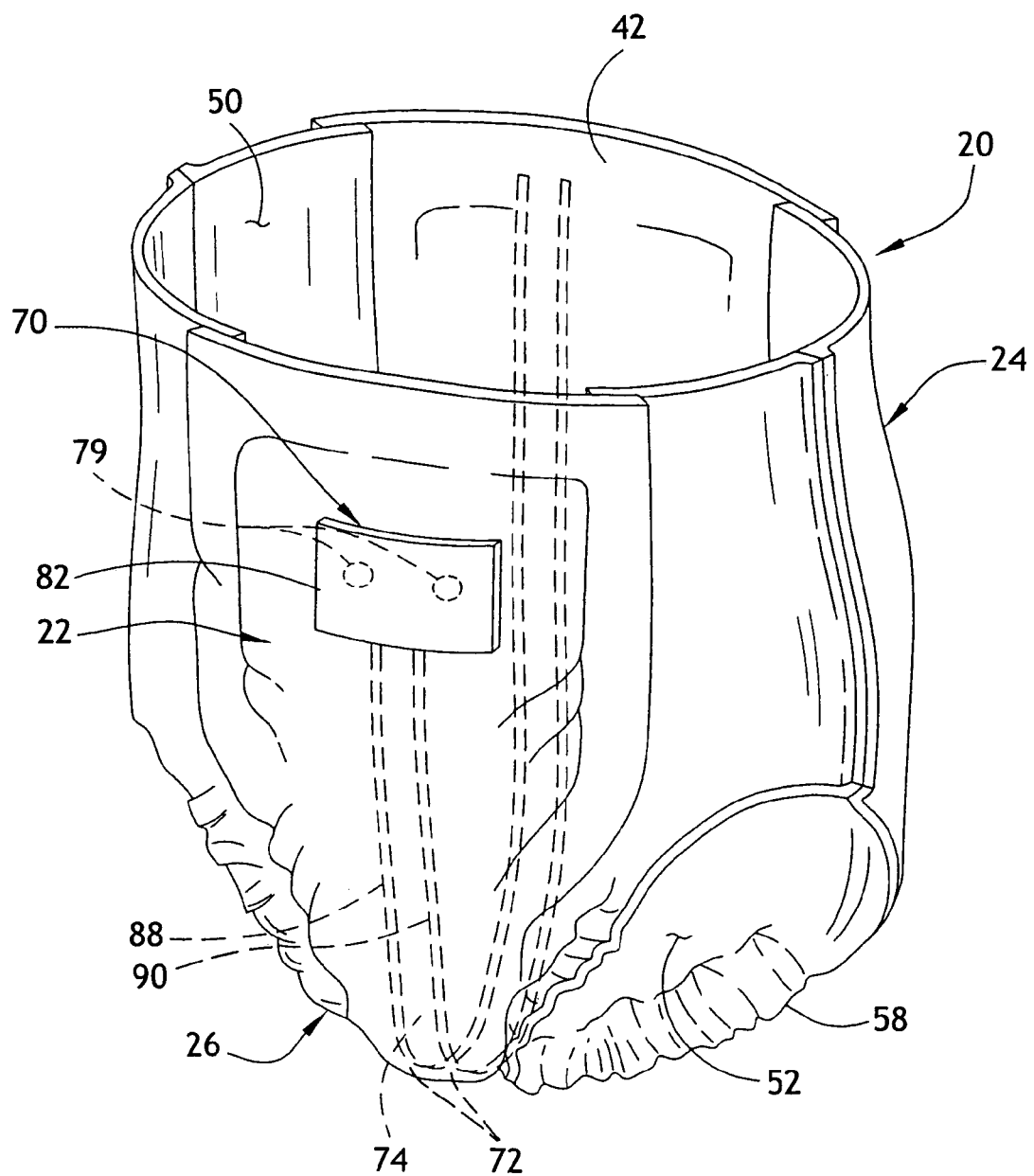
FIG. 2 is a perspective view of the pants of FIG. 1.
Figure 3:
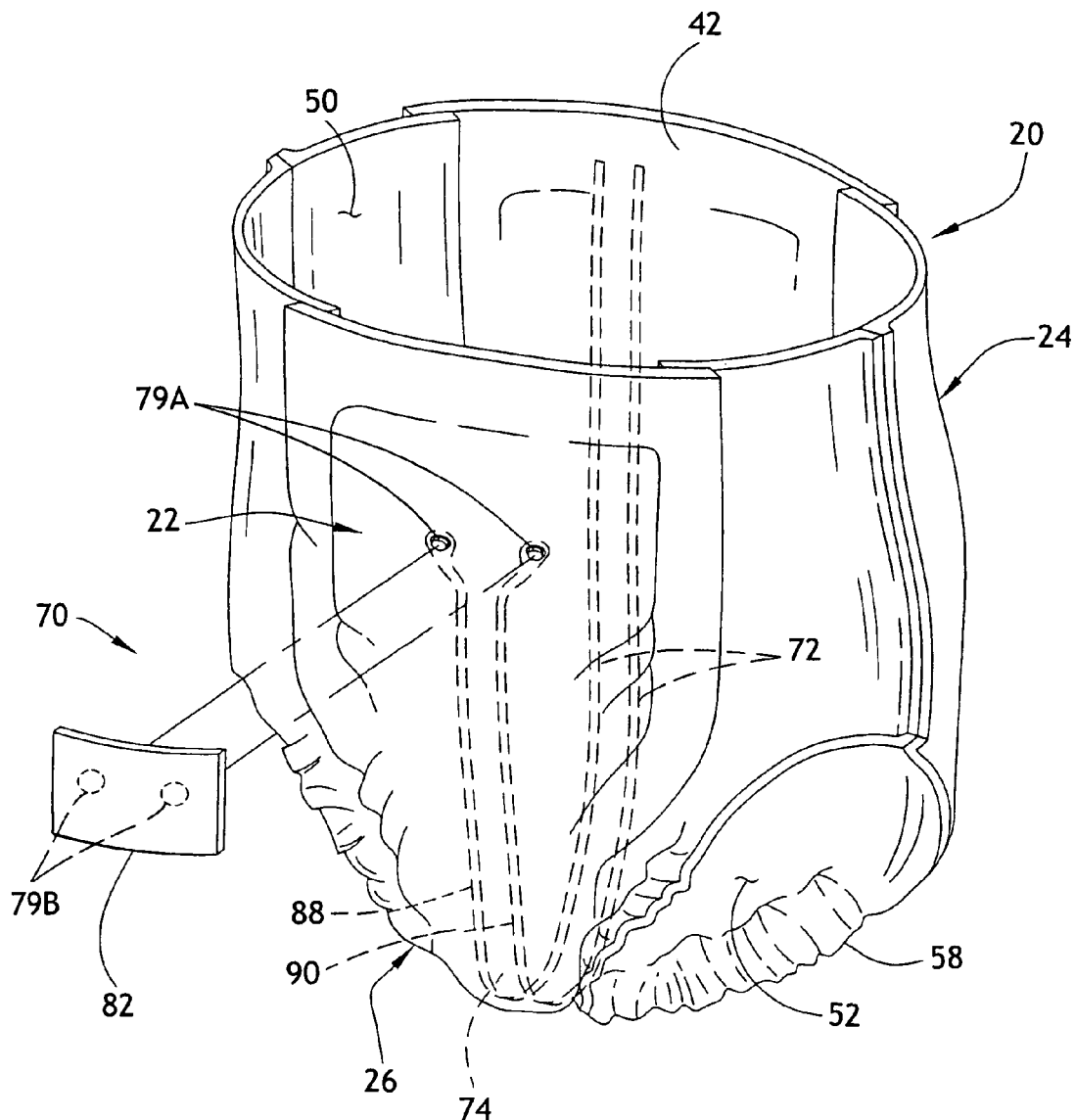
FIG. 3 is a perspective view of the pants similar to FIG. 2 showing the housing of a monitoring system removed from the article.

The absorbent assembly 32 is illustrated in FIGS. 1-3 as having a rectangular shape. However, it is contemplated that the absorbent assembly 32 may have other shapes (e.g., hourglass, T-shaped, I-shaped, and the like) without departing from the scope of this invention. It is also understood that the side panels 34A, 34B may instead be formed integrally with the absorbent assembly 32 without departing from the scope of this invention.

Figure 5:
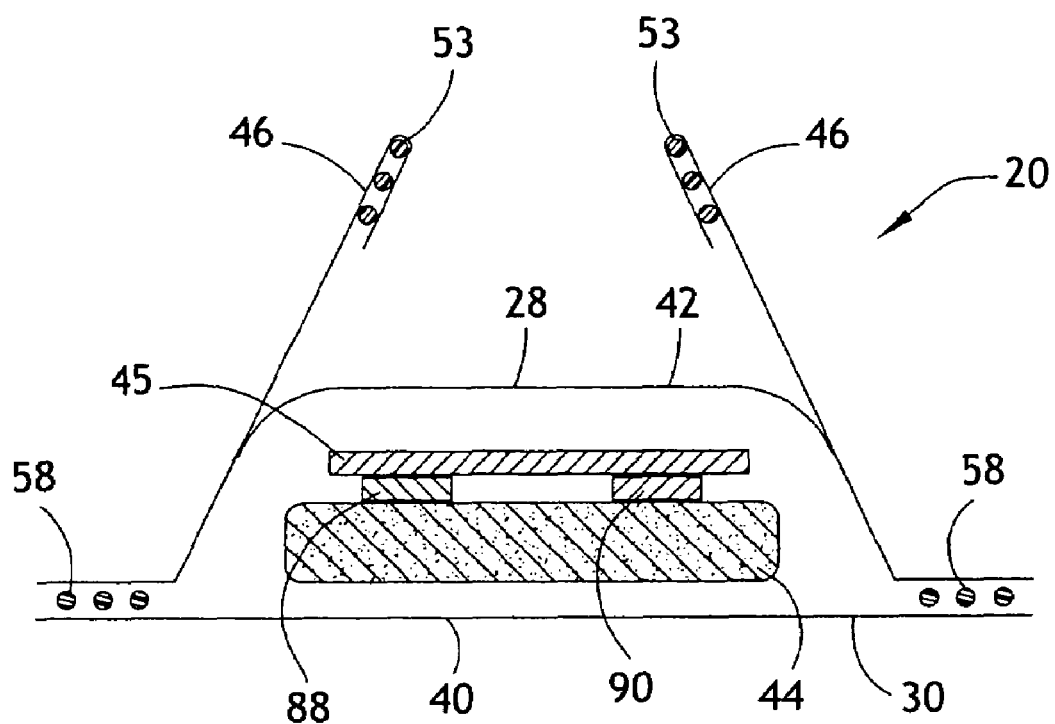
FIG. 5 is cross-sectional view of the pants of FIG. 4 taken along the line 5-5.

As shown best in FIGS. 4 and 5, the absorbent assembly 32 comprises an outer cover 40 and a bodyside liner 42 attached to the outer cover 40 in a superposed (opposed) relation therewith by adhesives, ultrasonic bonds, thermal bonds, pressure bonds, or other conventional techniques. The liner 42 is suitably joined to the outer cover 40 along at least a portion of the longitudinal ends of the pants 20. In addition, the liner 42 is suitably joined to the outer cover 40. The liner 42 is suitably adapted, i.e., positioned relative to the other components of the pants 20, for contiguous relationship with the wearer's skin during wear of the pants. The absorbent assembly 32 also comprises an absorbent structure 44 disposed between the outer cover 40 and the bodyside liner 42 for absorbing liquid body exudates exuded by the wearer and a surge management layer 45 disposed between the absorbent structure and the bodyside liner. A pair of containment flaps 46 is secured to the bodyside liner 42 for inhibiting the lateral flow of body exudates.

With the training pants 20 in the fastened position as partially illustrated in FIG. 1, the front and back waist regions are connected together by the fastening system 59 to define the three-dimensional pants configuration having a waist opening 50 and a pair of leg openings 52. The front and back waist edges 38 and 39 (e.g., longitudinal ends) of the training pants 20 are configured to encircle the waist of the wearer to define the waist opening 50 (FIG. 1) of the pants.

As illustrated in FIG. 4, a flap elastic member 53 can be operatively joined with each containment flap 46 in any suitable manner as is well known in the art. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may comprise a front waist elastic member 54 (FIG. 1), a rear waist elastic member 56, and leg elastic members 58 (FIGS. 2-4), as are known to those skilled in the art. The flap elastic members 53, the waist elastic members 54 and 56, and the leg elastic members 58 can be formed of any suitable elastic material that is well known to those skilled in the art.

The fastening system 59 of the illustrated embodiment comprises laterally opposite first fastening components 60 adapted for refastenable engagement to corresponding laterally opposite second fastening components 62. In one embodiment, a front or outer surface of each of the fastening components 60, 62 comprises a plurality of engaging elements. The engaging elements of the first fastening components 60 are adapted to repeatedly engage and disengage corresponding engaging elements of the second fastening components 62 to releasably secure the pants 20 in its three-dimensional configuration. The fastening components 60, 62 can comprise any refastenable fasteners suitable for absorbent articles, such as adhesive fasteners, cohesive fasteners, mechanical fasteners, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 suitably comprises a material that is substantially liquid impermeable. The outer cover 40 may comprise a single layer of liquid impermeable material, or more suitably comprise a multi-layered laminate structure in which at least one of the layers is liquid impermeable. While it is not a necessity for the outer layer to be liquid permeable, it is suitable that it provides a relatively cloth-like texture to the wearer. Alternatively, the outer cover 40 may comprise a woven or nonwoven fibrous web layer that has been totally or partially constructed or treated to impart the desired levels of liquid impermeability to selected regions that are adjacent or proximate the absorbent structure. The outer cover 40 may also be stretchable, and in some embodiments it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outer cover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. The bodyside liner 42 may also be stretchable, and in some embodiments it may be elastomeric. Reference is made to U.S. patent application Ser. No. 09/563,417 filed on May 3, 2000 by Roessler et al., U.S. patent application Ser. No. 09/698,512 filed on Oct. 27, 2000 by Vukos et al., both of which are incorporated by reference herein, for additional information regarding bodyside liner material.

The absorbent structure 44 is disposed between the outer cover 40 and the bodyside liner 42, which can be joined together by any suitable means such as adhesives, ultrasonic bonds, thermal bonds, or the like. While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents, or the like, as well as combinations thereof.

The materials may be formed into an absorbent web structure by employing various conventional methods and techniques known in the art. For example, the absorbent structure 44 may be formed by a dry-forming technique, an air-forming technique, a wet-forming technique, a foam-forming technique, or the like, as well as combinations thereof. Methods and apparatus for carrying out such techniques are well known in the art. The absorbent structure 44 may alternatively comprise a coform material such as the material disclosed in U.S. Pat. No. 4,100,324 to Anderson, et al.; U.S. Pat No. 5,284,703 to Everhart, et al.; and U.S. Pat. No. 5,350,624 to Georger, et al.; which are incorporated herein by reference.

Optionally, a substantially liquid permeable wrapsheet (not shown) may surround the absorbent structure 44 to help maintain the integrity of the absorbent structure 44.

Superabsorbent material is suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter. Superabsorbent materials are well known in the art and can be selected from natural, synthetic, and modified natural polymers and materials.

In one embodiment, the absorbent structure 44 may be stretchable so as not to inhibit the stretchability of other components to which the absorbent structure may be adhered, such as the outer cover 40 and bodyside liner 42. For example, the absorbent structure may comprise materials disclosed in U.S. Pat. Nos. 5,964,743, 5,645,542, 6,231,557, 6,362,389, and international patent application WO 03/051254, the disclosure of each of which is incorporated by reference herein.

The surge management layer 45 may be attached to various components of the article 20 such as the absorbent structure 44 and/or the bodyside liner 42 by methods known in the art, such as by adhesive, ultrasonic or thermal bonding. The surge management layer 45 helps to decelerate and diffuse surges or gushes of liquid that may be rapidly introduced into the absorbent structure 44 of the article 20. Desirably, the surge management layer 45 can rapidly accept and temporarily hold the liquid prior to releasing the liquid into the storage or retention portions of the absorbent structure 44. Examples of suitable surge management layers 45 are described in U.S. Pat. No. 5,486,166; and U.S. Pat. No. 5,490,846. Other suitable surge management materials are described in U.S. Pat. No. 5,820,973. The entire disclosures of these patents are incorporated by reference herein.

In general, the monitoring systems of the present invention comprise an insult circuit (also referred to herein as a wetness circuit). The insult circuit generally includes one or more conductors, a current source and a measuring device. The measuring device measures an electrical property of the insult circuit, e.g., resistance, conductance, voltage, etc., and sends a signal containing information regarding the electrical property to a microprocessor. The microprocessor analyzes the signal to determine if an insult has occurred. If an insult has occurred, an indicator is activated to signal a caregiver and/or wearer of the absorbent article of the presence of the insult.

In the illustrated embodiments, the training pants 20 of the present invention include a wetness monitoring system for detecting the presence of urine (broadly, an insult) within the pants 20. As illustrated in FIGS. 2-4, an exemplary wetness monitoring system is generally indicated by reference numeral 70. The monitoring system 70 includes a sensor 72 for detecting the electrical property (e.g., resistance R) of the article. The sensor 72 includes a pair of spaced apart generally parallel conductors 88, 90 disposed within the pants 20 that define a monitoring area 74 of the pants disposed between the conductors. The conductors 88, 90 may be constructed of any material that is generally electrically conductive. For example, the conductors may be constructed of metal strips (e.g., aluminum strips), metal films, coated films, conductive polymers, conductive inks, conductive threads, or the like, or combinations thereof. Other conductors are within the scope of this invention. As illustrated, the conductors 88, 90 extend longitudinally from the front waist region 22, through the crotch region 26, to the back waist region 24 of the pants 20. As shown best in FIG. 5, the conductors 88, 90 are disposed within the absorbent assembly 32 between the absorbent structure 44 and the surge management layer 45, although the conductors may be disposed at other locations without departing from the scope of this invention.

Figure 6:
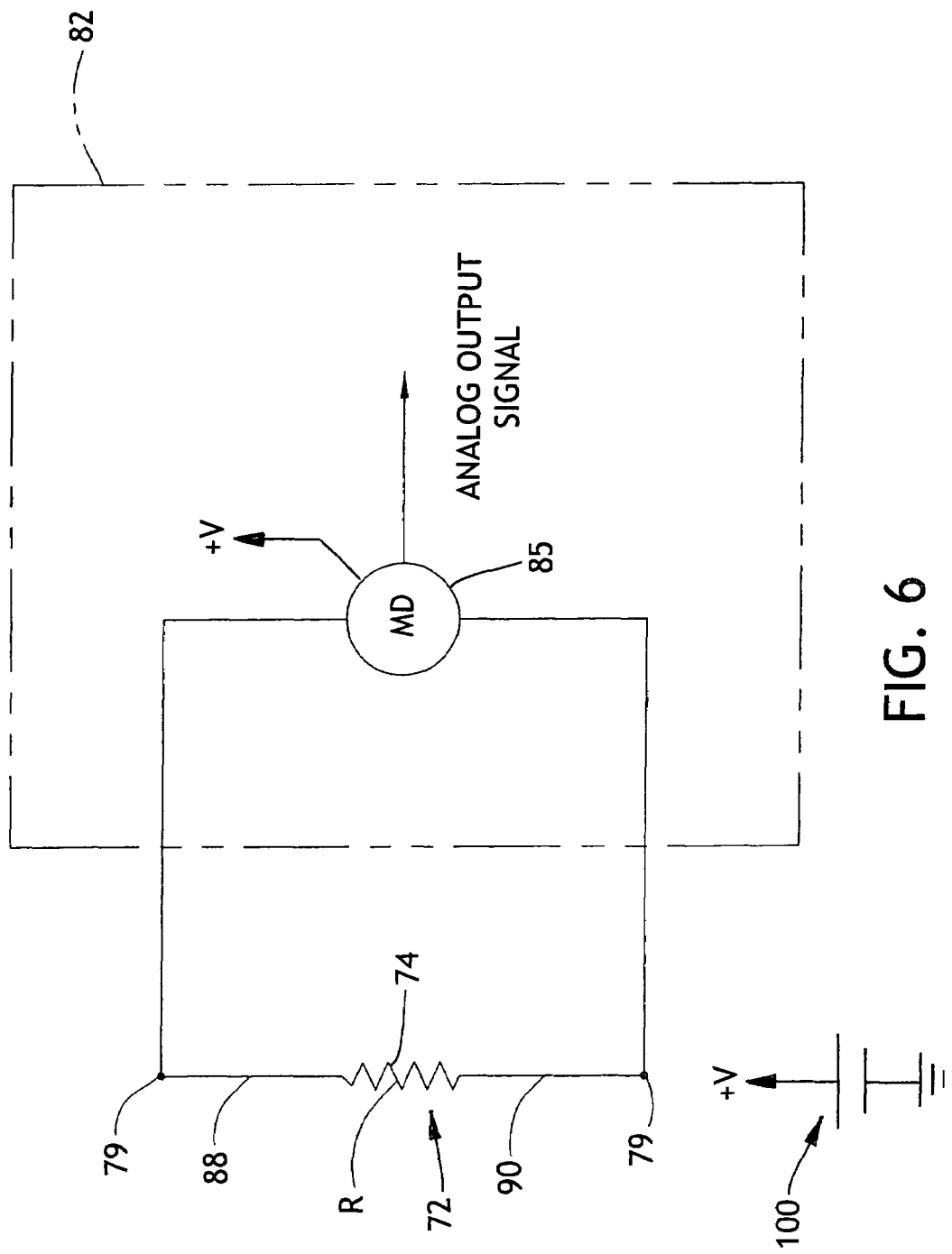
FIG. 6 is a schematic illustration of the pants and one embodiment of a wetness monitoring system of the present invention.

Current from a current source 100 (illustrated schematically in FIG. 6) runs through the conductors 88 and 90 of the sensor 72. The current source 100 may be a direct current source such as a battery (as illustrated), or an alternating current source. The conductors 88 and 90 may be electrically connected to the current source by any suitable contacts. For example, the contacts of the current source may be electrically connected with the conductors 88, 90 through one or more orifices located in one or more materials of the absorbent article. Alternatively or additionally, the contacts of the current source may pierce through one or more materials of the absorbent article to electrically connect with the conductors 88, 90. In the illustrated embodiment of FIGS. 2 and 3, the conductors 88, 90 are electrically connected to the current source by way of electrically conductive snap fasteners 79. However, any suitable means of electrically connecting the conductors to the current source are within the scope of this disclosure such as, for example, a clamp connector, conductive hook and loop fasteners, conductive adhesives (e.g., conductive tape), electrically conductive contacts, and the like, and combinations thereof. Suitable methods of electrically connecting the conductors to the current source are disclosed in commonly assigned U.S. patent application Ser. No. 11/303,283 to Long et al., filed on Dec. 15, 2005, entitled "Garments With Easy-To-Use Signaling Device" and U.S. patent application Ser. No. 11/303,222 to Mosbacher et al., filed on Dec. 15, 2005, entitled "Garments With Easy-To-Use Signaling Devices", the entirety of each are incorporated herein by reference where not contradictory.

As used herein, the term "electrically connected" or "electric connection" or derivatives thereof describes two or more objects positioned and/or configured such that current may flow to or from one object to the second object. In other words, these terms refer to a first contact, conductor, circuitry, or the like, being positioned and/or configured such that current may flow to or from a second contact, conductor, circuitry, or the like. In some embodiments, an electrical connection may also be a physical connection, such as through snaps, hooks, or the like. In some embodiments, an electrical connection may include two or more contacts, conductors, circuitry, that are touching, and therefore allow current to flow, but are not physically connected together.

As will be apparent from the discussion herein, the components of the monitoring system (e.g., measuring device, current source, microprocessor, analog-to-digital converter, indicator, transmitter, and/or receiver, etc.) may be housed together or separately, and may be attached to the absorbent article or may be present at a remote location. For example, in one embodiment, the measuring device, microprocessor, current source, analog-to-digital converter, and/or transmitter are housed together and are attached to the absorbent article, while the receiver and/or indicator are housed together at a remote location. As used herein, "remote location" means the components are not attached to the absorbent article. For example, in one embodiment, the receiver and/or indicator may be housed in a transportable unit that may be kept with the caregiver. Examples of such a unit may include an alarm such as a bed side alarm, alarm clock, beeper, or pager, a lamp, a wall clock, and the like.

As illustrated in FIGS. 2 and 3, each corresponding end of each conductor 88, 90 of the sensor 72 is electrically and physically connected to a first snap fastener member 79A located in the front waist region 22 of the pants 20. In some embodiments, the first snap fastener member may be located in the back waist region 24, or other locations on the pants 20.

A housing 82 that houses a current source 100 has corresponding second snap fastener elements 79B for engaging the first snap fasteners 79A and securing the housing to the pants 20. In addition to the current source 100, the housing 82 of the present embodiment may also house the remaining components of the wetness monitoring system 70 that will be described hereinafter, although it is contemplated that the housing may include only some or none of the remaining components. In the illustrated embodiment, the housing 82 is releasably secured to the pants 20 by way of the snap fasteners 79, although it is understood that the housing may be releasably secured to the pants 20 by other fasteners, such as for example, receptacles, adhesives, cohesives, magnets, hooks and loops, clips, clamps, snaps, pockets, straps, and the like, and combinations thereof. Alternatively, the housing may be permanently secured to the pants by any suitable means without departing from the scope of this invention.

A measuring device 85 (FIG. 6), electrically connected with the sensor 72, measures an electrical property of the monitoring area 74 of the pants 20. In one embodiment, the resistance, R, of the monitoring area 74 of the pants 20 is measured. Because the conductors 88, 90 are spaced apart, current from the current source 100 must pass through the monitoring area 74 to complete the circuit. As illustrated schematically in FIG. 6, the monitoring area 74 acts essentially as a resistor, as representatively indicated by reference character R. When the monitoring area 74 is dry (e.g., before the presence of an insult), the resistance of the monitoring area is relatively high, for example, some resistance above 200 k$\Omega$. When the monitoring area 74 is wetted, for example by an insult, its resistance drops, for example, to some resistance less than 200 K$\Omega$ (kilo ohms) because of the electrically conductive nature of urine.

In various embodiments, the conductors 88 and 90 may be connected by any suitable resistor or resistors located in the monitoring area 74, such as, for example, a chemiresistor to complete the circuit. Suitable chemiresistors are taught in U.S. patent application Ser. No. 11/314,438 to Dong et al., filed Dec. 21, 2005, entitled "Personal Care Products With Microchemical Sensors For Odor Detection", the entirety of which is incorporated herein by reference where not contradictory.

In another embodiment, the conductance of the monitoring area 74 of the pants 20 may be measured. As stated above, urine is electrically conductive and the article 20 generally is not electrically conductive. Therefore, when the monitoring area 74 of the pants 20 is wetted, its conductance is greater than when it is dry. Other electrical properties of the pants 20, including impedance, may be measured without departing from the scope of this invention.

The measuring device 85 produces an analog output signal (FIG. 6) indicative of the electrical property of the monitoring area 74 of the pants 20. For example, the measuring device 85 can measure a voltage drop across the monitoring area 74, and produce an analog output signal corresponding to the voltage drop. The output voltage signal can be used to determine other electrical properties, such as resistance or current, by performing suitable calculations known in the art or using a reference table. For example, as is well known in the art, the voltage drop is indicative of the resistance of the pants when the current is constant. Thus, the resistance of the pants 20 may be determined using the analog output signal of the measuring device 85. In various embodiments, the measuring device may be integral with a microprocessor or may provide an output signal to a microprocessor.

In various embodiments, any suitable method may be used to determine the presence (or lack thereof) of an insult in the absorbent article. For example, suitable methods are disclosed in U.S. patent application Ser. No. 11/215,937 to Long et al., filed on Aug. 31, 2005, entitled "Method Of Detecting The Presence Of An Insult In An Absorbent Article And Device For Detecting The Same"; U.S. patent application Ser. No. 11/216,977 to. Collins et al., filed on Aug. 31, 2005, entitled "Method Of Detecting The Presence Of Insults In An Absorbent Article"; and U.S. patent application Ser. No. 11/215,968 to Collins et al., filed on Aug. 31, 2005, entitled "Method Of Detecting The Presence Of An Insult In An Absorbent Article", the entirety of each are incorporated herein by reference where not contradictory.

In various embodiments, the monitoring system of the present invention may include an operational notification system. For the monitoring system to be operational, there must be sufficient current to the microprocessor and there must be an electrical connection between the microprocessor and the sensor associated with the absorbent article. Whereas, the monitoring system alerts the caregiver and/or the wearer as to the presence of an insult, the operational notification system alerts the caregiver and/or the wearer as to the status of the monitoring system. In other words, the operational notification system provides an indication as to whether the monitoring system is operational or non-operational. This notification assures the wearer and/or caregiver that the wetness monitoring system is ready to function as designed.

In general, the operational notification system comprises at least one continuity monitoring circuit. The continuity monitoring circuit generally includes at least one conductor associated with an absorbent article and a measuring device associated with a monitor. In the illustrated embodiments, the absorbent articles include two conductors, however, any suitable number of conductors may be utilized. The measuring device measures an electrical property of the continuity circuit, e.g., resistance, conductance, voltage, etc., and sends a signal containing information regarding the electrical property to a microprocessor. The microprocessor analyzes the signal to determine if there is electrical connection between the conductors in the absorbent article and the monitor. If an electrical connection exists, an indicator is activated to signal (i.e., notify) the caregiver and/or wearer of the absorbent article that the monitoring system is operational.

Figure 7:
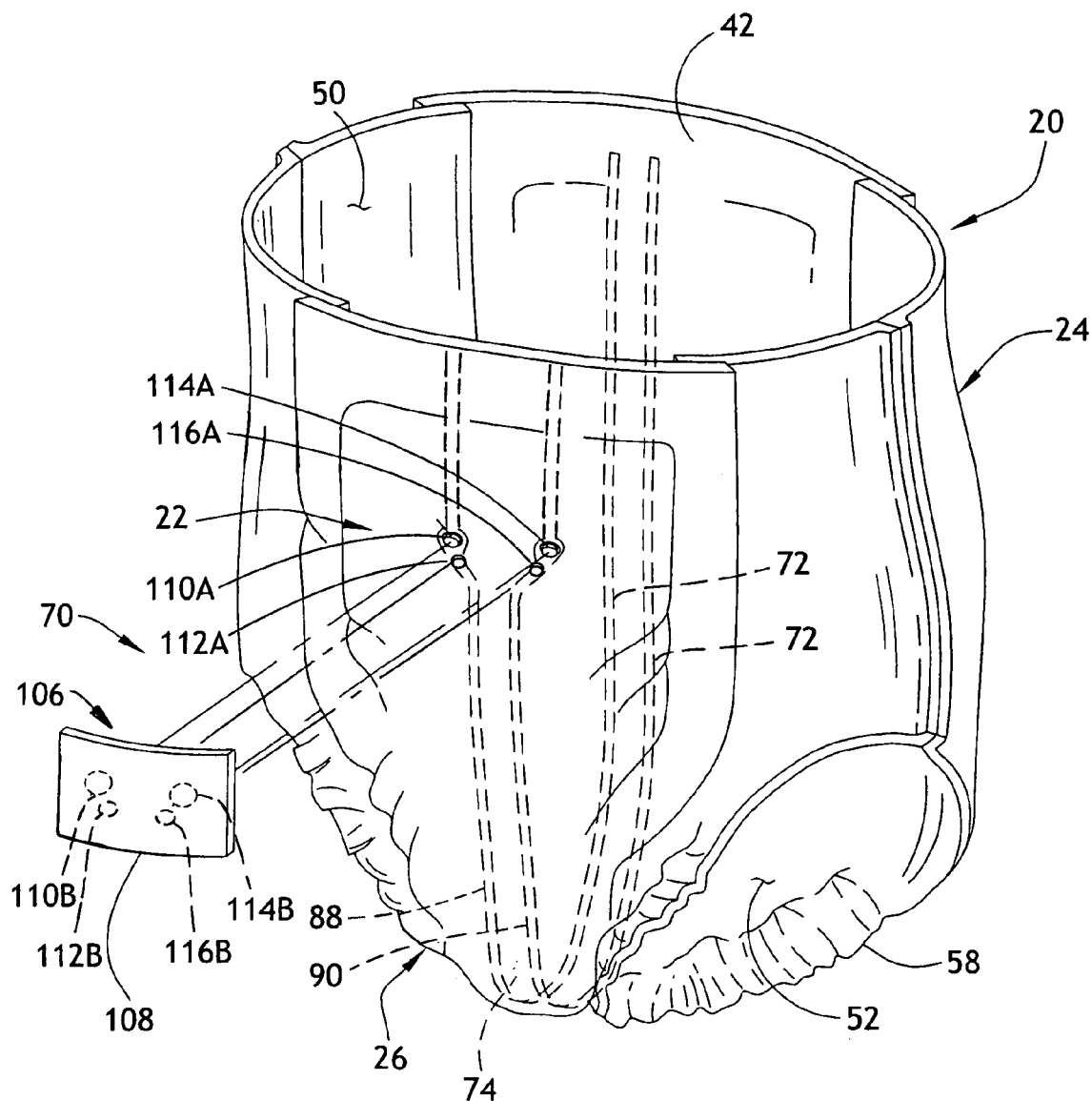
FIG. 7 is a perspective view of a wetness monitoring system, including an article and monitor, of the present invention.
Figure 8:
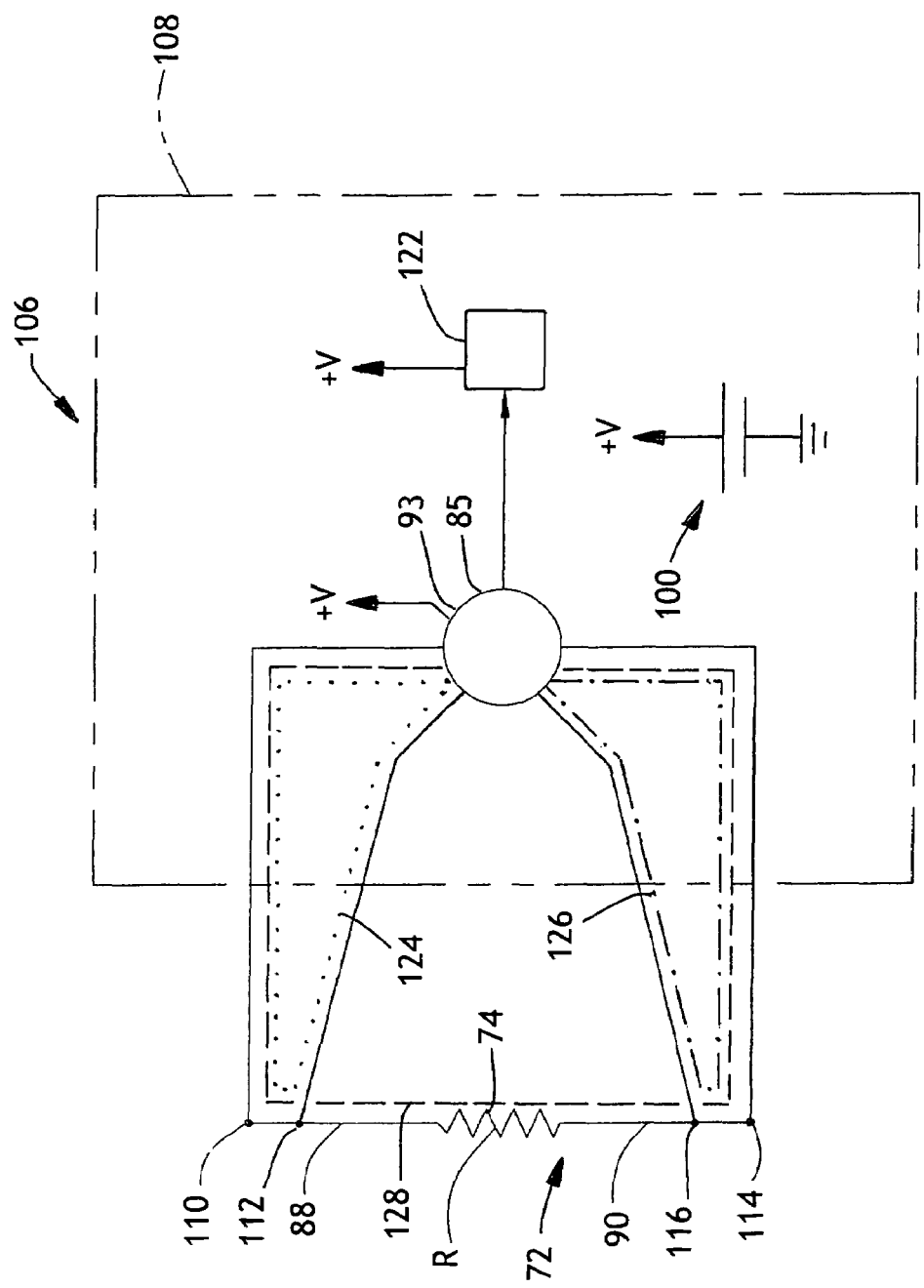
FIG. 8 is a schematic illustration of an exemplary wetness monitoring system and continuity monitoring system of the present invention.

FIG. 7 representatively illustrates an exemplary embodiment of a monitoring system including an operational notification system indicated generally at 106. The operational notification system 106 includes a monitor housing 108 (referred to hereinafter as the monitor) a portion of a first continuity monitoring circuit 124, a portion of a second continuity monitoring circuit 126, and a portion of a wetness monitoring circuit 128 as schematically illustrated in FIG. 8. In the illustrated embodiment, the monitor 108 includes a current source 100, a microprocessor 93, and an indicator 122. In the illustrated embodiment, a measuring device 85 is integral with the microprocessor 93. The microprocessor 93 and measuring device 85 form part of the first continuity monitoring circuit 124, part of the second continuity monitoring circuit 126, and part of the wetness monitoring circuit 128.

The monitor 108 is adapted to physically attach with a training pant 20 having a wetness sensor 72. The monitor 108 is adapted to electrically connect with the wetness sensor 72. The wetness sensor 72 may include a first conductor 88 and a second conductor 90, as described herein, to form part of the wetness monitoring circuit 128, as described herein. When an electrical connection is made between the measuring device 85 and the conductors 88 and 90, the first and second continuity monitoring circuits 124 and 126 are completed and the operational notification system 106 provides a signal (i.e., notification) to the wearer and/or caregiver that the wetness monitoring system is operational. The signal may be visual, tactile, auditory, or combinations thereof as described herein.

As illustrated in FIG. 7, the first conductor 88 is electrically connected to a first contact 110A and a second contact 112A. The second conductor 90 is electrically connected to a third contact 114A and a fourth contact 116A. The contacts 110A, 112A, 114A, and 116A are illustrated as snap fastener members but may be any suitable electrical contacts such as, for example, metal pads, conductive hook and loop fasteners, conductive adhesives (e.g., conductive tape), and the like, and combinations thereof. The contacts may be located in the front waist region 22 of the pants 20, as illustrated, or any other suitable location. The monitor 108 has corresponding contacts 110B, 112B, 114B, and 116B for making an electrical connection at points 110, 112, 114, and 116. In the illustrated embodiment, the contacts also secure (i.e., physically attach) the monitor 108 to the training pant 20, although it is contemplated that the monitor 108 may be releasably secured to the pant 20 by any suitable means such as for example, receptacles, adhesives, cohesives, magnets, hooks and loops, clips, clamps, snaps, pockets, straps, and the like, and combinations thereof.

As illustrated in FIG. 8, the measuring device 85 of the microprocessor 93 measures an electrical property of the wetness monitoring circuit 128 (indicated by a dashed line) as previously discussed, an electrical property of the first continuity monitoring circuit 124 (indicated by a dotted line), and an electrical property of the second continuity monitoring circuit 126 (indicated by a dot-dash line). When an electrical connection is made between points 110 and 112 and the first conductor 88, the first continuity circuit 124 is completed. When an electrical connection is made between points 114 and 116 and the second conductor 90, the second continuity circuit 126 is completed. In various embodiments, the microprocessor 93 may activate the indicator 122 when the first continuity circuit 124 is complete, when the second continuity circuit 126 is complete, or when both the first and the second continuity circuits 124 and 126 are complete. In various embodiments, the microprocessor 93 may send a signal to a transmitter that in turn sends the signal to a receiver to activate an indicator 122 when the first continuity circuit 124 is complete, when the second continuity circuit 126 is complete, or when both the first and the second continuity circuits 124 and 126 are complete. When activated, the indicator 122 may be any suitable device for notifying the wearer and/or caregiver that the system is operational, such as, for example, a speaker that makes a noise, such as a beep or a light that illuminates. In one embodiment, the microprocessor 93 may be programmed to activate the indicator 122 when both the first and the second continuity monitoring circuits 124 and 126 are complete. The indicator 122 may produce an auditory sound, such as a "beep", for a relatively short period of time (1 second, for example) and the indicator 122 may illuminate a light continuously until one or both of the continuity monitoring circuits 124 and 126 are opened.

Figure 9:
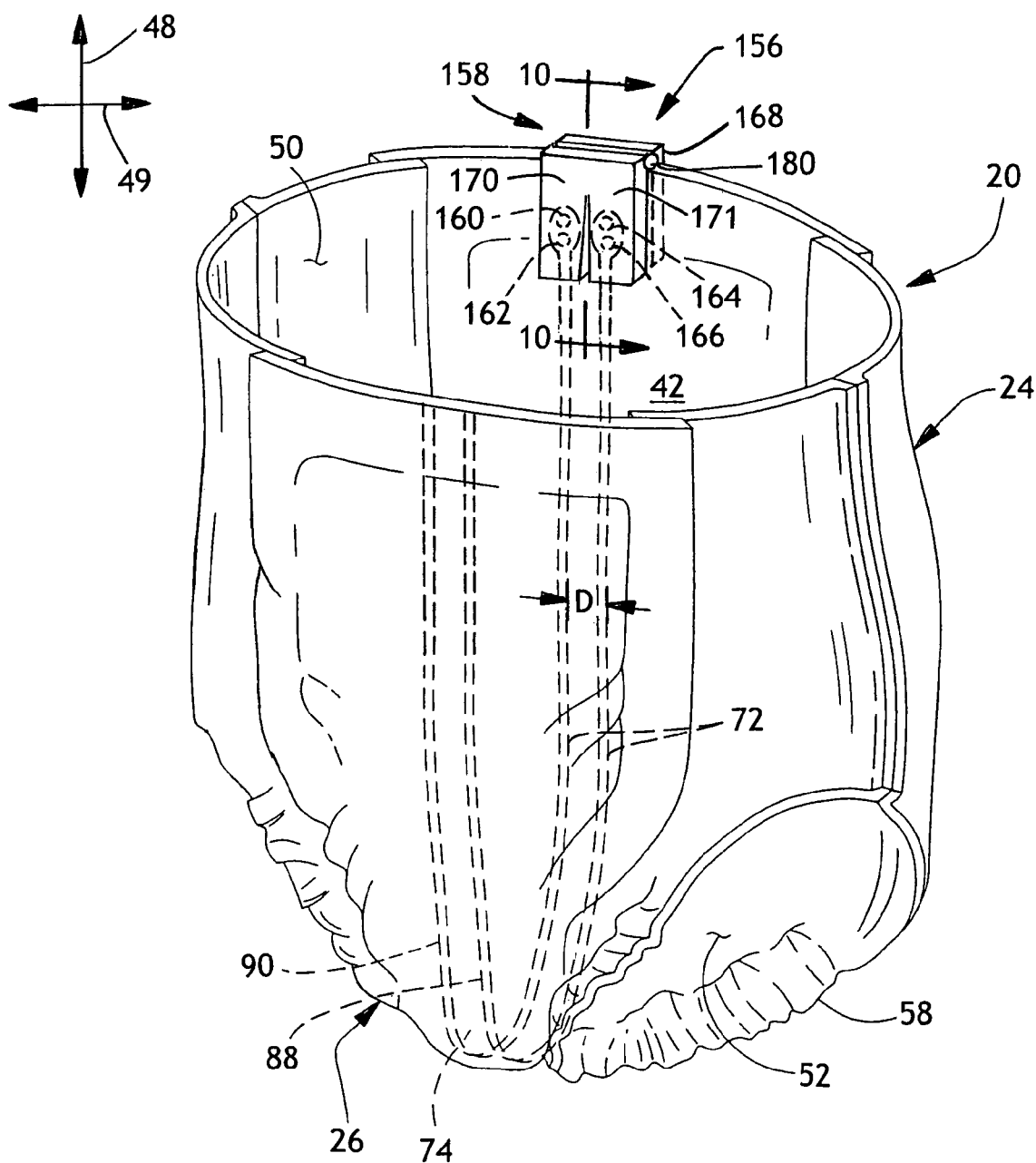
FIG. 9 is a perspective view of a wetness monitoring system, including an article and monitor, of the present invention.
Figure 10:
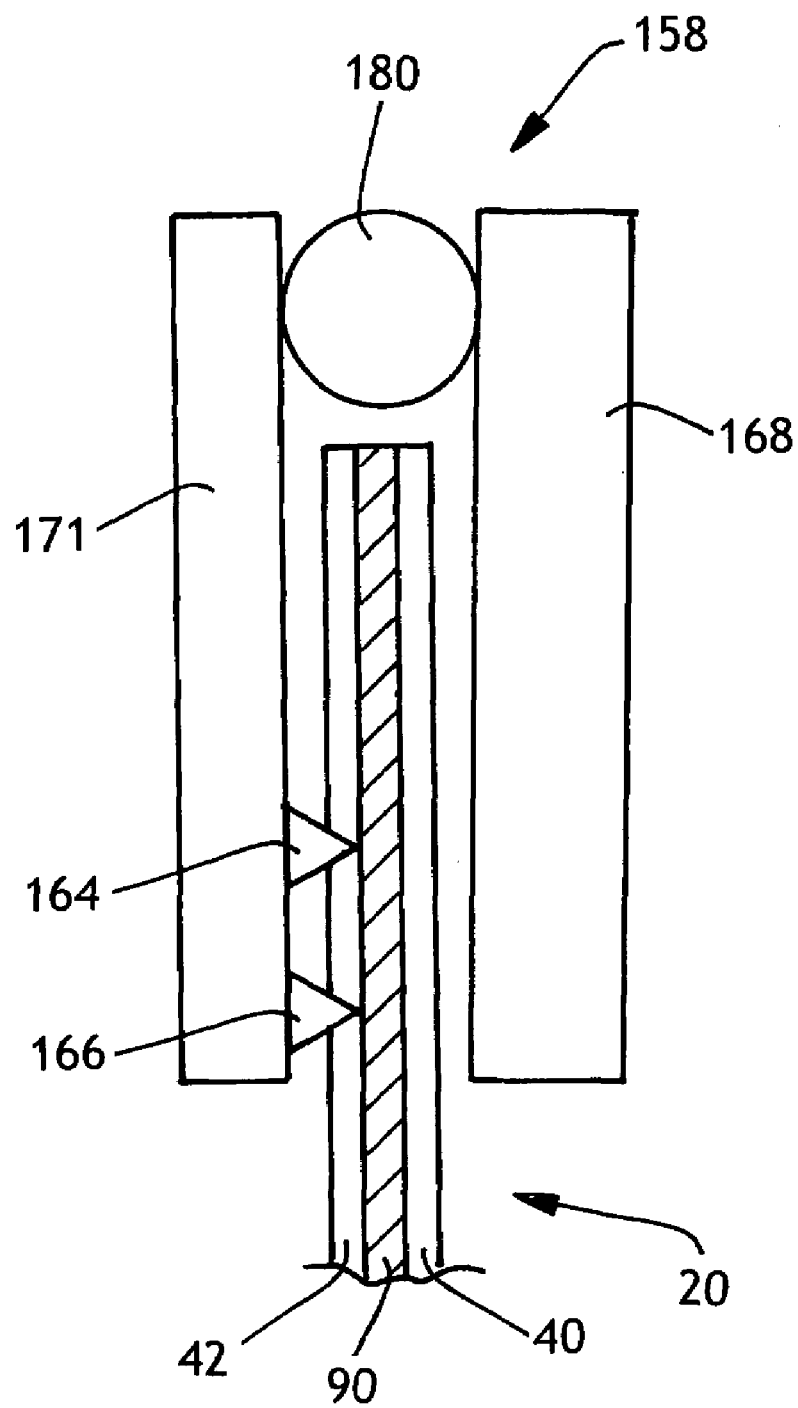
FIG. 10 is a cross-sectional view of the wetness monitoring system of FIG. 9 taken along the line 10-10.
Figure 11:
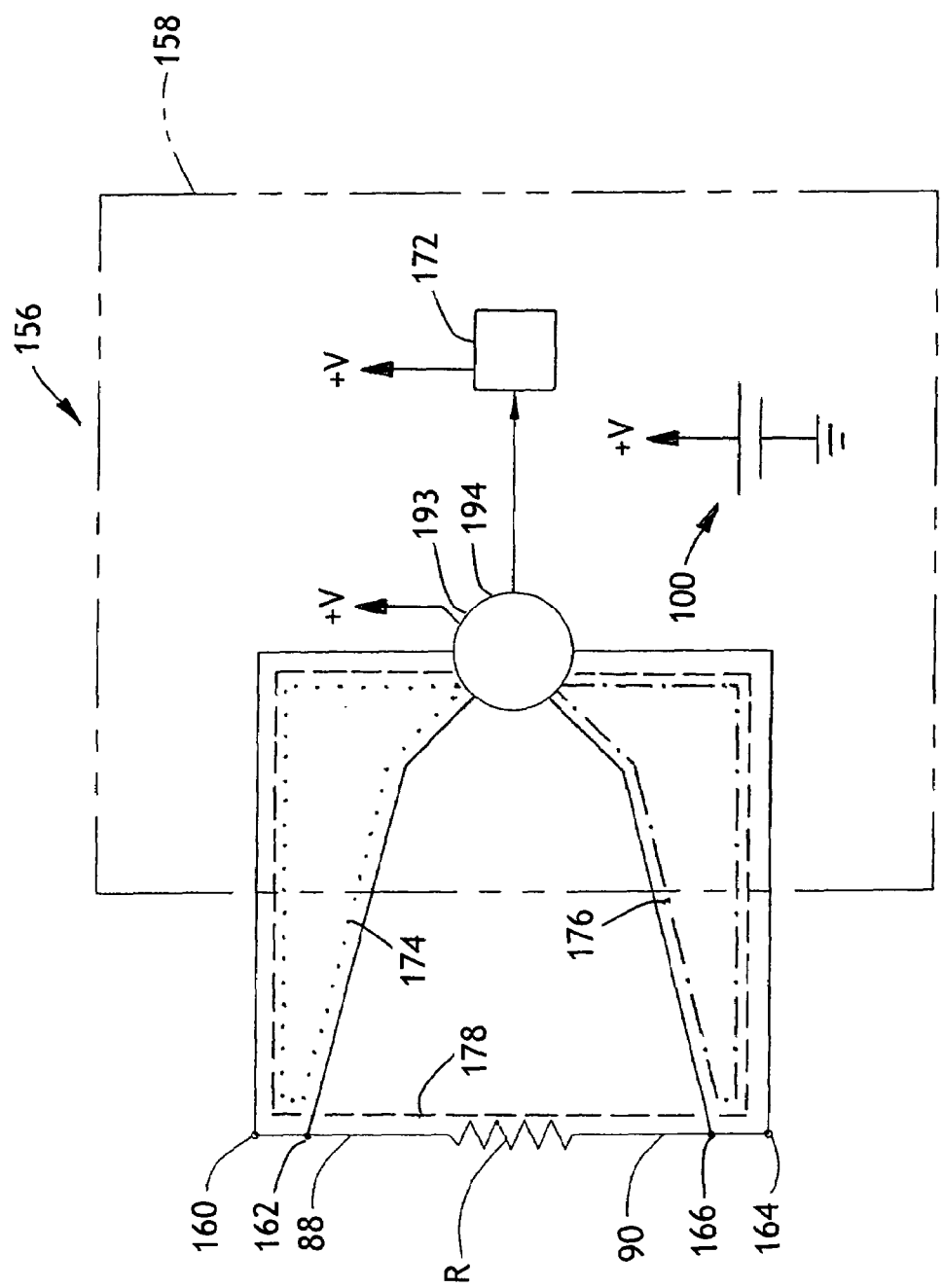
FIG. 11 is a schematic illustration of exemplary continuity monitoring circuits.

FIG. 9 representatively illustrates another exemplary embodiment of a monitoring system that includes an operational notification system 156 (schematically illustrated in FIG. 11). FIG. 10 representatively illustrates a cross-sectional view of FIG. 9 taken along the line 10-10. The operational notification system 156 of FIGS. 9, 10, and 11 is similar to the operational notification system 106 of FIG. 7 in that a monitor 158 is adapted to physically attach and electrically connect to a training pant 20 having a wetness sensor 72 disposed therein to complete a wetness monitoring circuit 178. The monitor 158 is adapted to attach to the training pant 20 to complete a first continuity monitoring circuit 174 and a second continuity monitoring circuit 176 as schematically illustrated in FIG. 11.

As illustrated in FIGS. 9 and 10, the monitor 158 is adapted to clip to the back waist region 24 of the absorbent article 20. The monitor 158 includes a first attachment leg 170, a second attachment leg 171, a main housing 168, and a hinge 180. The first and second attachment legs 170 and 171 are pivotally attached via the hinge 180 with the main housing 168 such that the monitor 158 can be transitioned from an open condition to a closed condition and a wearer and/or care giver may releasably attach the monitor 158 to the absorbent article 20.

The first attachment leg 170 includes a first contact 160 and a second contact 162 adapted to make an electrical connection with either the first conductor 88 or the second conductor 90. In the illustrated embodiment, the first contact 160 and the second contact 162 are aligned with first conductor 88 and are adapted to penetrate through the bodyside liner 42 to make an electrical connection with the first conductor 88. The second attachment leg 172 includes a third contact 164 and a fourth contact 166 adapted to make an electrical connection with the other conductor 88 or 90. In the illustrated embodiment, the third contact 164 and the fourth contact 166 are aligned with the second conductor 90 and are adapted to penetrate through the bodyside liner 42 to make an electrical connection with the second conductor 90.

In alternative embodiments, the bodyside liner 42 may have one or more openings located therein to allow access to the conductors 88 and/or 90 to facilitate making an electrical connection. In yet other embodiments, the outer cover 40 may be penetrated and/or may include openings located to facilitate an electrical connection between the contacts of the monitor and the conductors within the absorbent article.

Referring to FIG. 11, the monitor 158 includes a current source 100, a microprocessor 193, and an indicator 172. In the illustrated embodiment, a measuring device 194 is integral with the microprocessor 193. When an electrical connection is made between the measuring device 194 of the monitor 158 and the conductors 88 and 90 in the article, the operational notification system 156 provides a signal to the wearer and/or caregiver that the wetness monitoring system is operational. The signal may be visual, tactile, auditory, or combinations thereof.

The measuring device 194 of the microprocessor 193 measures an electrical property of the wetness monitoring circuit 178 (indicated by a dashed line), an electrical property of the first continuity monitoring circuit 174 (indicated by a dotted line), and an electrical property of the second continuity monitoring circuit 176 (indicated by a dot-dash line). When an electrical connection is made between the contacts 160 and 162 and the first conductor 88, the first continuity monitoring circuit 174 is completed. When an electrical connection is made between the contacts 164 and 166 and the second conductor 90, the second continuity monitoring circuit 176 is completed. In various embodiments, the microprocessor 193 may activate the indicator 172 when the first continuity circuit 174 is complete, when the second continuity circuit 176 is complete, or when both the first and the second continuity circuits 174 and 176 are complete. When activated, the indicator 172 may be any suitable device for notifying the wearer and/or caregiver that the system is operational, such as, for example, a speaker that makes a noise or a light that illuminates.

In various embodiments, the wetness sensor and the monitors are adapted to electrically connect in any suitable way. For example, as representatively illustrated in FIG. 9, the wetness sensor 72 may include a first conductor 88 and a second conductor 90 extending generally in a longitudinal direction 48. The first conductor 88 and second conductor 90 may be spaced apart in a lateral direction 49 by a distance, D. The monitor 158 may include a first contact 160 and a second contact 162 aligned generally in the longitudinal direction 48. The monitor 158 may include a third contact 164 and a fourth contact 166 aligned generally in the longitudinal direction 48. The first contact 160 and the second contact 162 may be spaced apart from the third contact 162 and the fourth contact 164 by a distance of about, D, as measured in the lateral direction 49 such that an electrical connection may be made with the first and second conductors 88 and 90.

The illustrated embodiments include two contacts per conductor wherein one or more contacts form part of more than one circuit. It is contemplated that, in various embodiments, one or more additional contacts may be utilized such that some or all of the contacts form part of only one circuit. For example, each conductor may be in electrical connection with three contacts wherein one of the contacts forms part of a wetness circuit but not part of a continuity circuit and two of the contacts form part of a continuity circuit but neither form part of the wetness circuit. In other words, each contact may be part of only one circuit.

In another exemplary embodiment of a monitoring system including an operational notification system, a monitor may be adapted to notify the wearer and/or caregiver when an electrical connection is made between the monitor and an absorbent article to which the monitor is attached. The notification may include one or more visual signals, tactile signals, auditory signals, or combinations thereof.

In this embodiment, a monitor includes a current source, a microprocessor, and a measuring device, such as, for example, those described herein. The monitor is adapted to function with any suitable absorbent article having any suitable sensor therein to complete any suitable wetness circuit, such as, for example, those described herein. For example, referring again to a wetness monitoring system like that illustrated in FIG. 3, the housing 82 may include a measuring device that is integral with a microprocessor. The microprocessor may be adapted to signal a wearer and/or a caregiver of one or more conditions, such as, for example, a non-operational condition, an operational condition and/or a wet condition, and the like.

Figure 12:
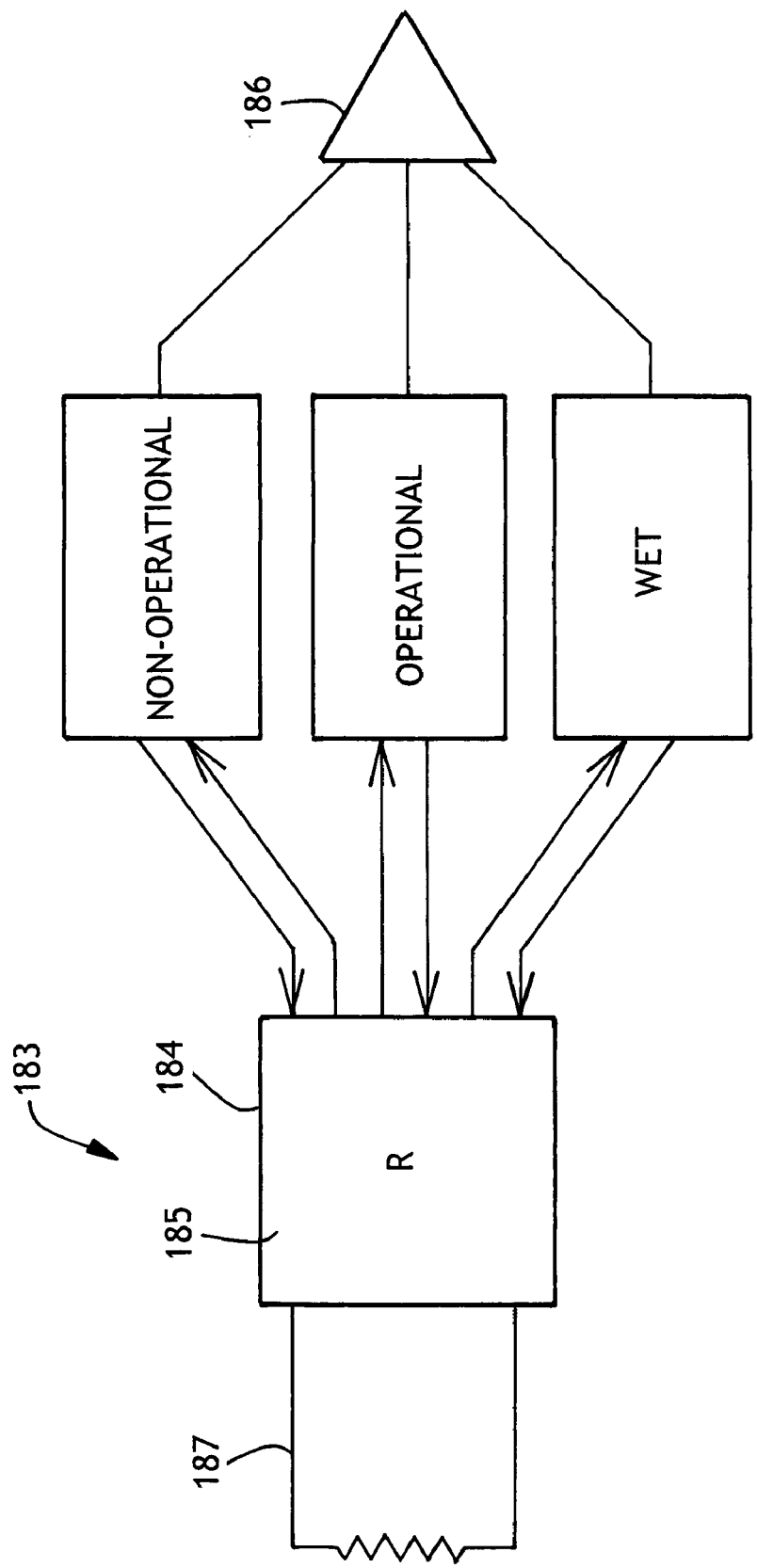
FIG. 12 schematically illustrates microprocessor flow logic for a wetness monitoring system.

FIG. 12 schematically illustrates the microprocessor flow logic for a wetness monitoring system 183 that includes an operational notification system. The measuring device 185 is programmed to periodically or continuously measure an electrical property, such as resistance, in a wetness circuit 187 as described herein. The microprocessor may further be programmed to provide a first indication when the electrical property is above a first value. For example, a resistance measurement, R, above some threshold, such as 10 MΩ may be interpreted by the microprocessor 184 as the wetness monitoring system 183 being in a non-operational condition i.e., the monitor is not attached to the absorbent article and/or the monitor is not in electrical contact with the conductors. In various embodiments, the microprocessor 184 may activate any suitable indicator 186 to provide the first indication. The first indication may provide notification to the wearer and/or care giver that the wetness monitoring system 183 is "non-operational."

The microprocessor may further be programmed to provide a second indication when the electrical property is below the first value and above a second value. For example, a resistance measurement, R, above a suitable threshold, such as, for example, 1 MΩ but below about 10 MΩ, may be interpreted by the microprocessor 186 as the wetness monitoring system 183 being in an operational condition, i.e., the monitor is in electrical contact with the conductors disposed within the absorbent article. In various embodiments, the microprocessor 186 may activate any suitable indicator 122 to provide the second indication. The second indication may provide notification to the wearer and/or care giver that the wetness monitoring system 183 is "operational."

The microprocessor may further be programmed to provide a third indication when the electrical property is below the second value. For example, a resistance measurement, R, below a suitable threshold, such as, for example, 60 kΩ, may be interpreted by the microprocessor 186 as the wetness monitoring system 183 being in a wet condition, i.e., an insult has been detected. In various embodiments, the microprocessor 186 may activate any suitable indicator 186 to provide the third notification. The third indication may provide notification to the wearer and/or caregiver that the wetness monitoring system 183 is "wet." As will be evident to those of skill in the art, after the microprocessor has interpreted the resistance measurements, and activated any suitable indicator, the microprocessor may continue to measure the electrical property of the wetness monitoring system.

The first, second, and/or third indications may be audio, visual, tactile, or the like. The first, second, and/or third indications may be the same or may be different. For example, the first indication may be a red light, the second indication may be a green light, and the third indication may be an audible alarm.

The circuits described and illustrated herein involve electrical connections. However, any of the circuits described herein, may also include one or more additional signaling "links" to the circuit as desired. For example, one or more optical sensors could be included in the circuits such that when placed over a foil conductor, an LED could produce light and the optical sensor could monitor for a reflection. Whether the reflected light is sensed or not, the monitor could produce a notification accordingly. Alternatively or additionally, when placed over a specific color, an LED that produced light could reflect that color to the optical sensor for proper alignment. Whether the reflected light is sensed or not, the monitor could produce an indication accordingly. Similarly, any of the circuits described herein may further include any other suitable signaling means, including magnetism, pressure, temperature, acceleration, strain, and the like, and combinations thereof.

In various embodiments, the microprocessors may be programmed to activate one or more indicators at various times, for various durations, via various means as will be evident to one skilled in the art. For example, in any suitable embodiment, the microprocessor may be programmed to provide a notification to the wearer and/or caregiver when the wetness monitoring system first becomes operational. In some embodiments, the microprocessor may be adapted to notify the wearer and/or caregiver that the wetness monitoring system is operational at any suitable interval by activating one or more indicators. In some embodiments, the Microprocessor may be programmed to provide notification to the wearer and/or caregiver when the wetness monitoring system becomes non-operational by activating one or more indicators. For example, the monitor may beep when continuity is detected, beep periodically while continuity is detected and beep when continuity is broken.

As will be evident to those skilled in the art, various indications may be produced through the same device or devices (i.e., indicators). For example, a single speaker may produce one or more "indications." The speaker may beep (first indication) when the continuity monitoring circuit is complete, the speaker may beep periodically (second indication) as the continuity monitoring circuit remains closed, and the speaker may sound an alarm (third indication) when wetness is detected.

In various embodiments, the monitoring system of the present invention may include an attachment notification system. The attachment notification system is adapted to alert the caregiver and/or the wearer as to whether the removable components of the monitoring system, e.g., a monitor housing, are securely attached to the absorbent article. For example, a monitor may be attached to an absorbent article having a wetness sensor such that an electrical connection is made between the monitor and the sensor but improper or incomplete physical attachment of the monitor to the absorbent article could jeopardize the likelihood of continued electrical connection. This is particularly important in executions involving training pants worn by active children wherein the monitor may become detached during use thereby rendering the wetness monitoring system non-functional. This too may be desirable in executions wherein the absorbent article includes lofty and/or thick materials and engagement of the monitor involves penetrating the article or clipping to the article. In these embodiments, the contacts may come into electrical connection with the conductors, but the clip may not be fully closed or the contacts may not be fully penetrated.

Therefore, the attachment notification system may be added to any embodiment described herein as a "second line of defense" beyond the operational notification system or may be utilized without an operational notification system. As the monitors may be attached to the absorbent articles in various suitable ways, the attachment notification system may also take various forms. In general, the attachment notification system includes one or more attachment monitoring circuits.

Figure 13:
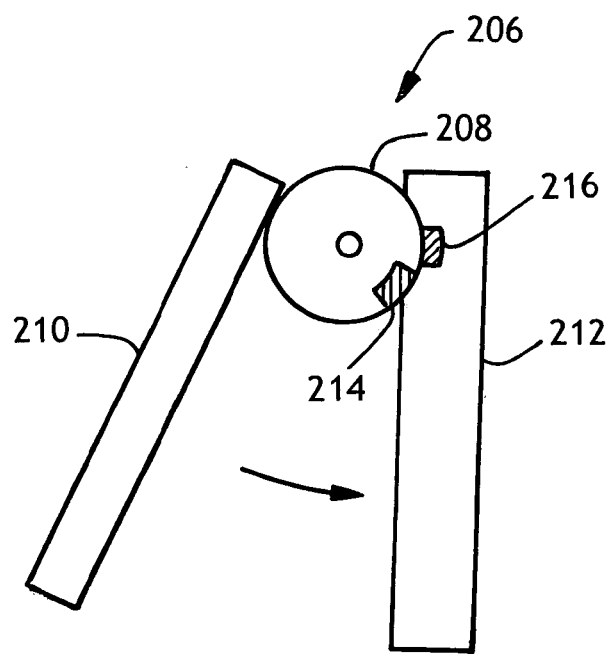
FIG. 13 is a cross-section view of an exemplary monitor.
Figure 14:
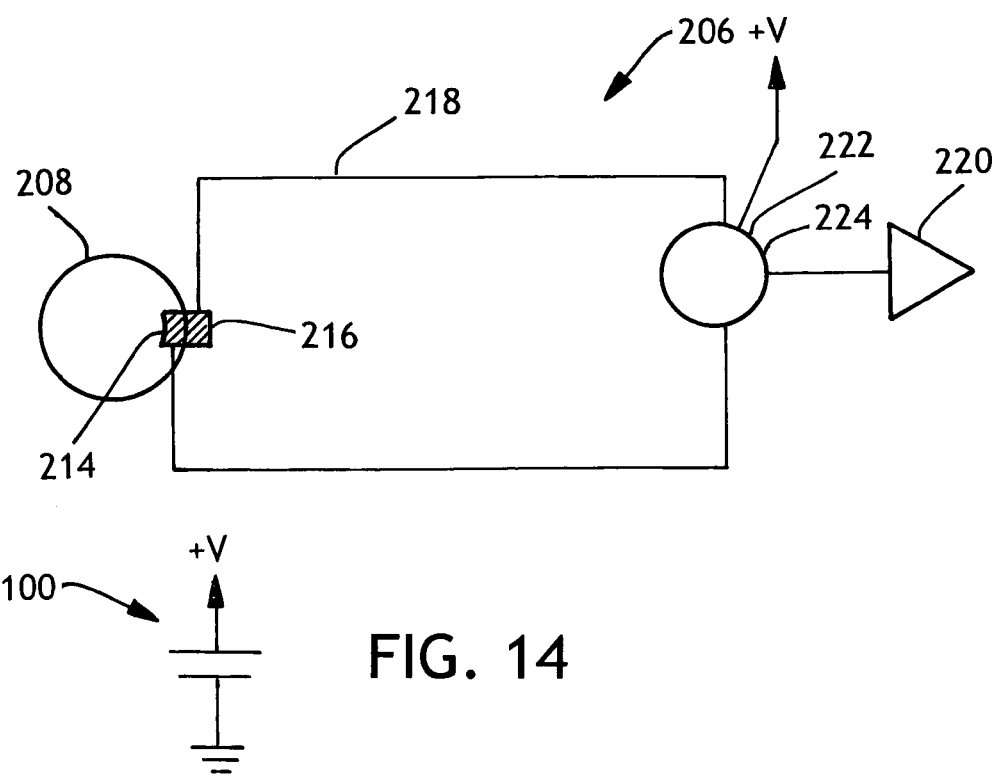
FIG. 14 schematically illustrates an attachment circuit of the monitor of FIG. 13.

FIG. 13 representatively illustrates an exemplary monitor 206 having an attachment notification system. The monitor 206 has an attachment leg 210 that is pivotally connected by a hinge 208 to a main housing 212. The hinge 208 has a first contact 214 and the main housing has a second contact 216. When the monitor 206 is in an open condition, as illustrated, the first contact 214 and the second contact 216 are not electrically connected. When the attachment leg 210 is pivoted shut via the hinge 208, the first contact 214 is brought into electrical connection with the second contact 216 thereby completing an attachment monitoring circuit 218 as schematically illustrated in FIG. 14. The attachment monitoring circuit 218 includes a microprocessor 222 with an integral measuring device 224 and a current source 100. When contacts 214 and 216 are brought into electrical connection, the attachment circuit 218 is completed and the microprocessor 222 may be programmed to activate an indicator 220 to notify the wearer and/or care giver that the monitor is securely attached to the absorbent article.

FIG. 15 representatively illustrates another exemplary monitor 230 having an attachment notification system. The monitor 230 has an attachment leg 232 that is pivotally connected by a hinge 234 to a main housing 236. The attachment leg 232 has a first contact 238 and a second contact 240. The main housing has a first receptacle 242 adapted to receive the first contact 238 in electrical connection and a second receptacle 244 adapted to receive the second contact 240 in electrical connection.

When the monitor 230 is in an open condition, as illustrated, the first contact 238 is not electrically connected with the first receptacle 242. Similarly, the second contact 240 is not electrically connected with the second receptacle 244. When the attachment leg 232 is pivoted shut via the hinge 234, the first contact 238 penetrates the bodyside liner 42, the conductor 246 and the outercover 40 to make an electrical connection with the first receptacle 242 thereby completing a first attachment circuit 248 as schematically illustrated in FIG. 16. Similarly, when the attachment leg 232 is pivoted shut via the hinge 234, the second contact 240 penetrates the bodyside liner 42, the conductor 246 and the outercover 40 to make an electrical connection with the second receptacle 244 thereby completing a second attachment circuit 250 as schematically illustrated in FIG. 16. The first and second contacts 238 and 240 may also be adapted to make an electrical connection with the conductor 246 located between a bodyside liner 42 and an outer cover 40 to form part of a continuity monitoring circuit similar to that illustrated in FIGS. 9, 10, and 11. The first and second contacts 238 and 240 may also be adapted to make an electrical connection with the conductor 246 located between a bodyside liner 42 and an outer cover 40 to form part of a wetness monitoring circuit similar to that illustrated in FIGS. 7 and 8. These circuits have been omitted from FIG. 16 for clarity.

In various embodiments, the first contact 238 and/or the second contact 240 may not penetrate the intervening materials and physically touch the receptacles to make an electrical connection. In some embodiments, the intervening materials may be pushed into the receptacles such that the contacts are in sufficient proximity to make an electrical connection.

The first and second attachment monitoring circuits 248 and 250 include a microprocessor 252 which may include an integral measuring device 254 and a current source 100. When contacts 238 and 240 are brought into electrical connection with receptacles 242 and 244, the attachment circuits 248 and 250 are completed and the microprocessor 252 may be programmed to activate an indicator 256 to notify the wearer and/or care giver that the monitor 230 is completely closed and therefore securely attached to the absorbent article.

In various embodiments, the microprocessor 252 may be programmed to activate the indicator 256 when the first attachment circuit 248 is complete, when the second attachment circuit 250 is complete, or when both the first and the second attachment circuits 248 and 250 are complete. When activated, the indicator 256 may be any suitable device for notifying the wearer and/or caregiver that the system is operational, such as, for example, a speaker that makes a sound or a light that illuminates.

In various embodiments, the microprocessor may be programmed with various instructions to allow continuous or intermittent monitoring and notification of the relevant circuits. For example, a microprocessor may be programmed to continuously and/or periodically monitor one or more circuits and provide one or more indications when the one or more circuits are opened and/or closed. The notification may be provided in some embodiments after a set period of time has elapsed. In other words, a circuit may have to be opened and/or closed for a certain length of time before the microprocessor activates an indicator. For example, a microprocessor may be programmed to monitor a continuity circuit and activate an indicator immediately upon detection of a completed circuit or may be programmed to activate an indicator after five seconds of detecting a completed circuit.

Wetness monitoring systems have traditionally had to balance the power needs of the system with the cost and life expectancy of the current source, e.g., a battery. Therefore, it is desirable to control the use of the battery by the various systems. For example, battery consumption is not controlled if a monitor is shipped from the manufacturer with the battery active. Uncontrolled battery consumption results in unpredictable shelf life and is further complicated by distribution timing, inventory management, and other factors often outside the control of the manufacturer. Therefore, in various embodiments, the current source may be part of a power management system. The power management systems may take various forms and generally include one or more power circuits.

As used herein, the term power management system describes a monitor having a current source and at least two different current flow conditions. Therefore, when the battery is dead there is no current source and therefore does not constitute a flow condition. For example, a monitor having a power management system may have a current source and an "off" condition wherein little or no current is flowing and an "on" condition wherein some greater amount of current is flowing. In some embodiments, the power management system may include additional conditions, such as, for example, a "power save" condition wherein some current is flowing but not as much as in the "on" condition.

An exemplary power management system may include a power circuit that includes an electrically insulated strip interrupting the power circuit. With the strip in place, little or no current is flowing and, therefore, the power management system is in the off condition. The insulating strip may be adapted to be removed by the wearer or caregiver prior to the first use. Removal of the insulating strip transitions the monitor from the off condition to the on condition by allowing current to flow throughout the power circuit from the current source. This power management system minimizes the impact of shipping, storage, and inventory control, but once the monitor is activated, the current continues to flow until the battery is exhausted.

In various embodiments, the present invention may also include a method of providing a power management system by providing a monitor with an electrically insulated strip interrupting the power circuit and instructing the wearer and/or user to remove the insulating strip from the power circuit to transition the monitor from the off condition to the on condition.

Another exemplary power management system includes a manually activated and deactivated power circuit. In this embodiment, the monitor may be adapted such that a wearer and/or caregiver may activate and deactivate the power circuit, i.e., transition the monitor from the off condition to the on condition (activate) or transition the monitor from the on condition to the off condition (deactivate). For example, the wearer may activate and deactivate the power circuit by manipulating a switch associated with the monitor housing. In some embodiments, the switch may be located on an external surface of the monitor for easy access. Any suitable type of switch may be utilized to transition the power circuit from opened to closed and from closed to opened.

FIG. 17 representatively illustrates a manually activated and deactivated power circuit 270 that includes a switch 272 and a current source, such as, for example, a battery 274. The manually activated and deactivated power circuit 270 may be utilized with any suitable monitor 276 and any suitable wetness monitoring system 278, such as, for example, those disclosed herein among others. When the wearer and/or caregiver manually closes the switch 272 and completes the power circuit 270, current flows to the monitor 276 and the monitoring system 278. In other words, the wearer and/or caregiver transitions the monitor from the off condition to the on condition. Similarly, when the wearer and/or caregiver opens the switch 272, the manually activated and deactivated power circuit 270 is deactivated and the current stops flowing and the battery 274 is conserved. In other words, the wearer and/or caregiver transitions the monitor from the on condition to the off condition.

In various embodiments, the switch 272 may be positioned at any suitable location on the monitor. For example, the switch 272 may be positioned on an external surface of the monitor such that the wearer and/or caregiver may access the switch 272 as desired to conserve the battery 274.

In various embodiments, the present invention may further include providing a monitor having a manually activated and deactivated power management system, providing instructions to manually close the switch to complete the power circuit and transition the monitor to the on condition, and providing instructions to manually open the switch to disconnect the power circuit and transition the monitor to the off condition.

Another exemplary power management system includes the use of an integrally activated and deactivated power circuit. The integrally activated and deactivated power circuit is similar to the manually activated and deactivated power described above in that a power circuit is opened or closed by a switch. However, in the integrally activated and deactivated power circuit, the wearer and/or caregiver activates the power circuit "automatically" when attaching the monitor to the absorbent article. Likewise, in the integrally activated and deactivated power circuit, the wearer and/or caregiver deactivates the power circuit "automatically" when detaching the monitor from the absorbent article. Therefore, the battery is preserved when not in use and the wearer and/or caregiver does not need to perform an additional step and cannot forget to activate or deactivate the power circuit.

Figure 18:
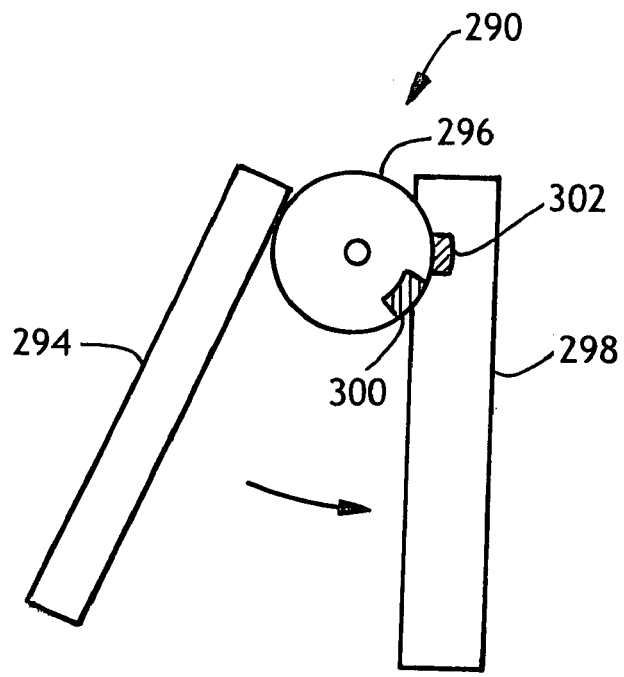
FIG. 18 is a side view of an exemplary monitor.
Figure 19:
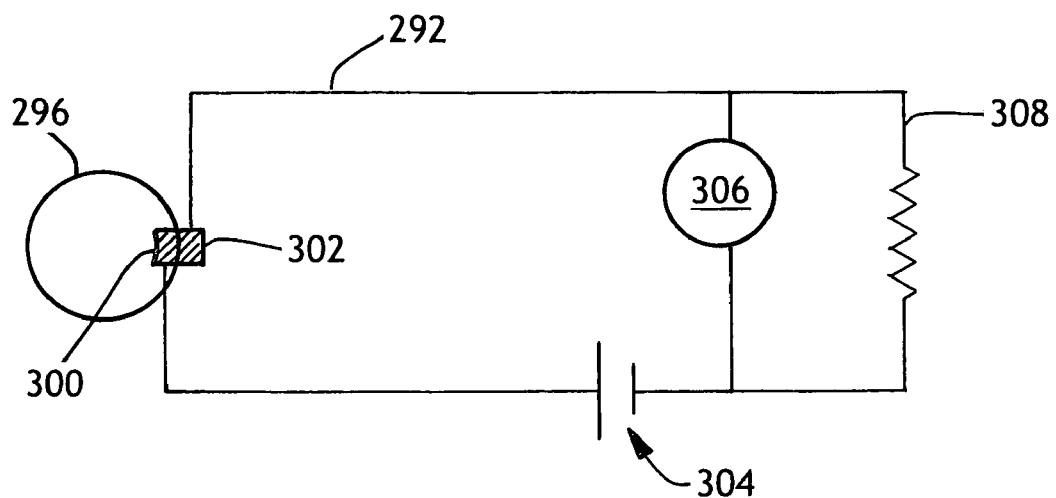
FIG. 19 schematically illustrates a power management circuit of the monitor of FIG. 18.

FIG. 18 representatively illustrates an exemplary monitor 290 having an integrally activated and deactivated power circuit. The monitor 290 has an attachment leg 294 that is pivotally connected by a hinge 296 to a main housing 298. The hinge 296 has a first contact 300 and the main housing has a second contact 302. When the monitor 290 is in an open condition, as illustrated, the first contact 300 and the second contact 302 are not electrically connected. When the attachment leg 294 is pivoted shut via the hinge 296, the first contact 300 is brought into electrical connection with the second contact 302 thereby completing the integrally activated and deactivated power circuit 292 as schematically illustrated in FIG. 19. The integrally activated and deactivated power circuit 292 includes a current source, such as, for example, a battery 304, a microprocessor 306 and a monitoring system 308. When contacts 300 and 302 are brought into electrical connection, the integrally activated and deactivated power circuit 292 is completed and the current from the battery 304 can flow to the microprocessor 306 and the monitoring system 308.

Figure 20:
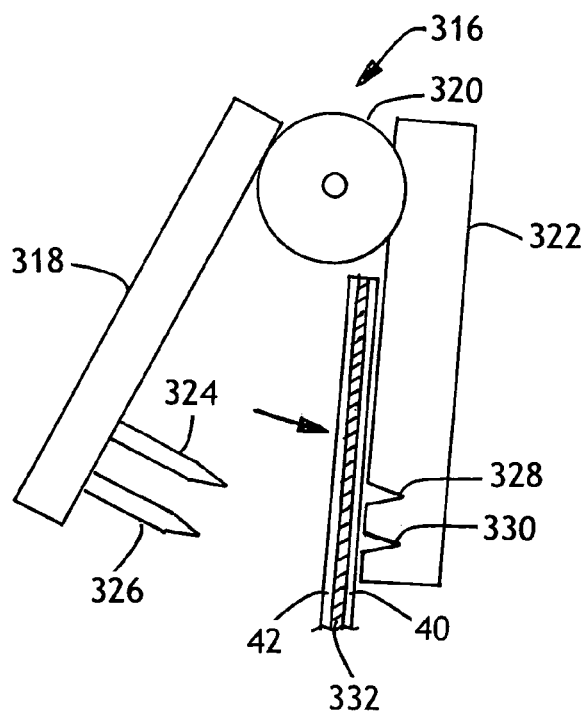
FIG. 20 is a side view of an exemplary monitor.

FIG. 20 representatively illustrates another exemplary monitor 316 having an integrally activated and deactivated power circuit. The monitor 316 has an attachment leg 318 that is pivotally connected by a hinge 320 to a main housing 322. The attachment leg 318 has a first contact 324 and a second contact 326. The main housing has a first receptacle 328 adapted to receive the first contact 324 in electrical connection and a second receptacle 330 adapted to receive the second contact 326 in electrical connection.

Figure 21:
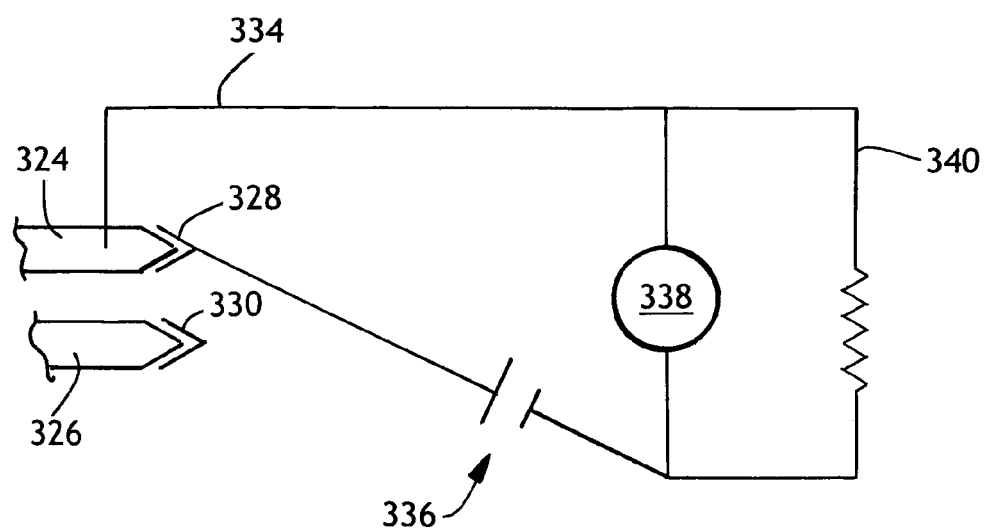
FIG. 21 schematically illustrates a power management circuit of the monitor of FIG. 20.

When the monitor 316 is in an open condition, as illustrated in FIG. 20, the first contact 324 is not electrically connected with the first receptacle 328. Similarly, the second contact 326 is not electrically connected with the second receptacle 330. When the attachment leg 318 is pivoted shut via the hinge 320, the first contact 324 makes an electrical connection with the first receptacle 328 thereby completing an integrally activated and deactivated power circuit 334 as schematically illustrated in FIG. 21. The integrally activated and deactivated power circuit 334 includes a current source, such as, for example, a battery 336, a microprocessor 338 and a monitoring system 340. When the first contact 324 and the first receptacle 328 are brought into electrical connection, the integrally activated and deactivated power circuit 334 is completed and the current from the battery 336 can flow to the microprocessor 338 and the monitoring system 340. Those skilled in the art will appreciate that the integrally activated and deactivated power circuit could alternatively include the second contact 326 and the second receptacle 330.

The various systems described herein may be utilized in any suitable combination with any suitable monitoring system. For example, a monitor may include any suitable power management system, any suitable attachment notification system, and any suitable operational notification system in conjunction with any suitable wetness monitoring system, such as, for example, the various systems described herein.

Figure 22:
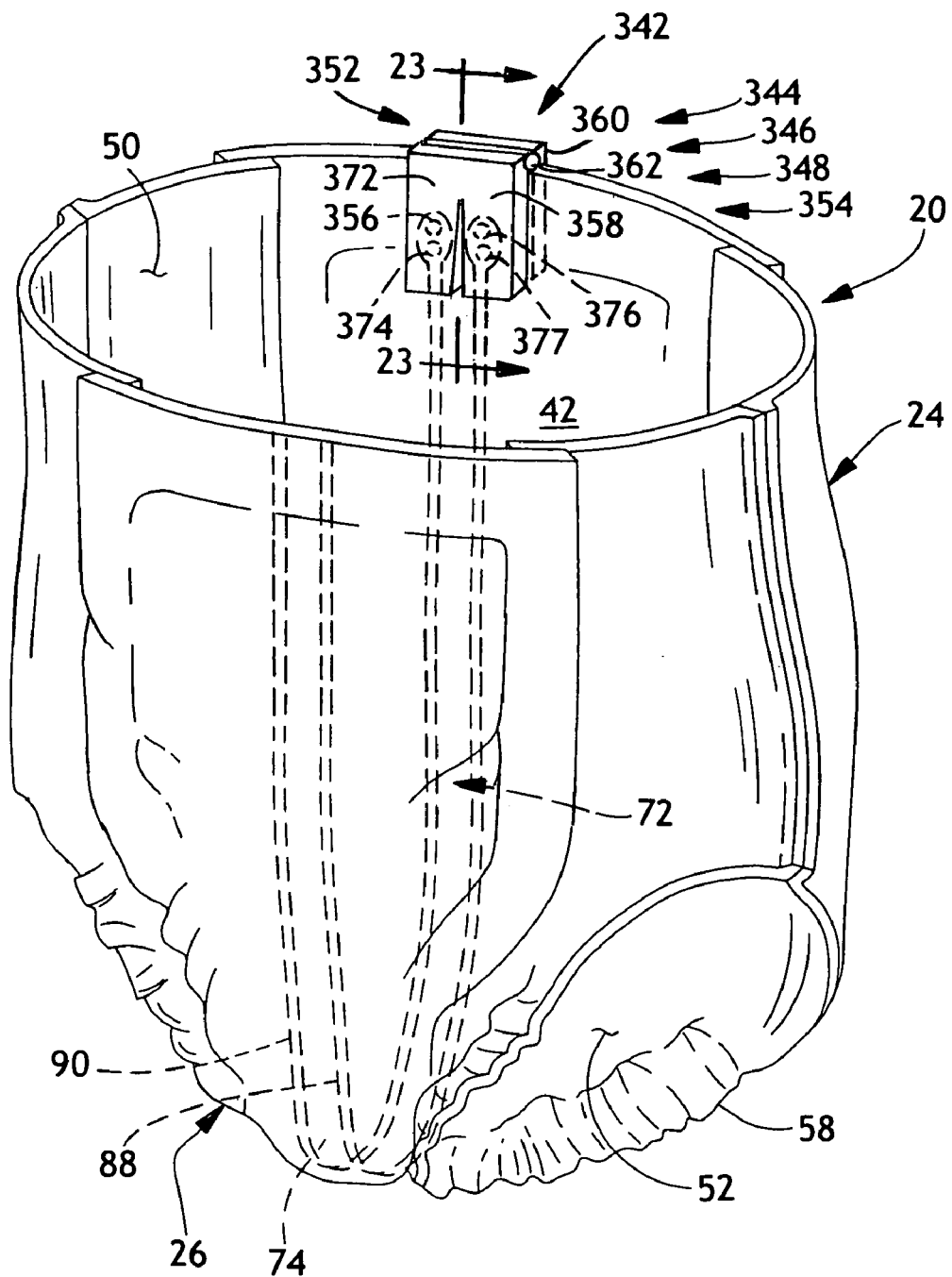
FIG. 22 is a perspective view of a wetness monitoring system, including an article and a monitor, of the present invention.

For example, FIG. 22 representatively illustrated an exemplary embodiment of a monitoring system 342 that includes an operational notification system 344, an attachment notification system 346, and a power management system 348. The monitoring system 342 includes a monitor 352 adapted to attach to a training pant 20 having a wetness sensor 72 disposed therein to complete a wetness monitoring circuit 354. The wetness sensor 72 includes a first conductor 88 and a second conductor 90.

The monitor 352, as illustrated, is adapted to clip to the back waist region 24 of the absorbent article 20. The monitor 352 includes a first attachment leg 356, a second attachment leg 358, a main housing 360, and a hinge 362. The first attachment leg 356 and the second attachment leg 358 are pivotally connected, via the hinge 362, with the main housing 360 such that the wearer and/or care giver may releasably attach the monitor 352 to the absorbent article 20. The monitor 352 is adapted to attach to the training pant 20 to complete a first continuity circuit 364, a second continuity circuit 366, an attachment circuit 368 and a power circuit 370 as schematically illustrated in FIG. 24.

Figure 23:
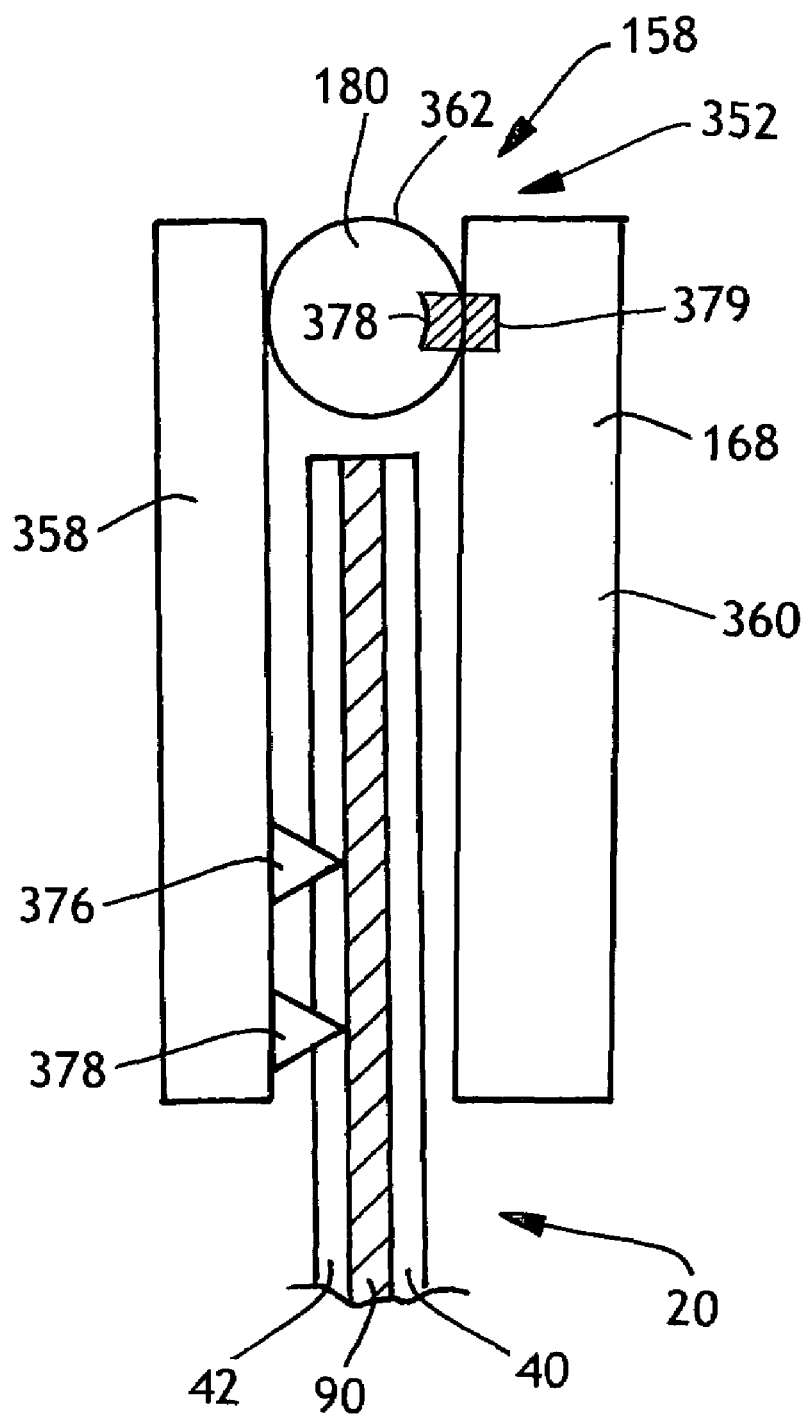
FIG. 23 is a cross-sectional view of the wetness monitoring system of FIG. 22 taken along the line 23-23.

FIG. 23 representatively illustrates a cross-sectional view of the monitoring system of FIG. 22 taken along the line 23-23. Referring to FIGS. 22 and 23, the first attachment leg 356 includes a first contact 372 and a second contact 374 adapted to make an electrical connection with either the first conductor 88 or the second conductor 90. In the illustrated embodiment, the first contact 372 and the second contact 374 are aligned with first conductor 88 and are adapted to penetrate through the bodyside liner 42 to make an electrical connection with the first conductor 88. The second attachment leg 358 includes a third contact 376 and a fourth contact 378 adapted to make an electrical connection with the other conductor 88 or 90. In the illustrated embodiment, the third contact 376 and the fourth contact 377 are aligned with the second conductor 90 and are adapted to penetrate through the bodyside liner 42 to make an electrical connection with the second conductor 90. The hinge 362 includes a fifth contact 378 and the main housing 360 includes a sixth contact 379.

Figure 24:
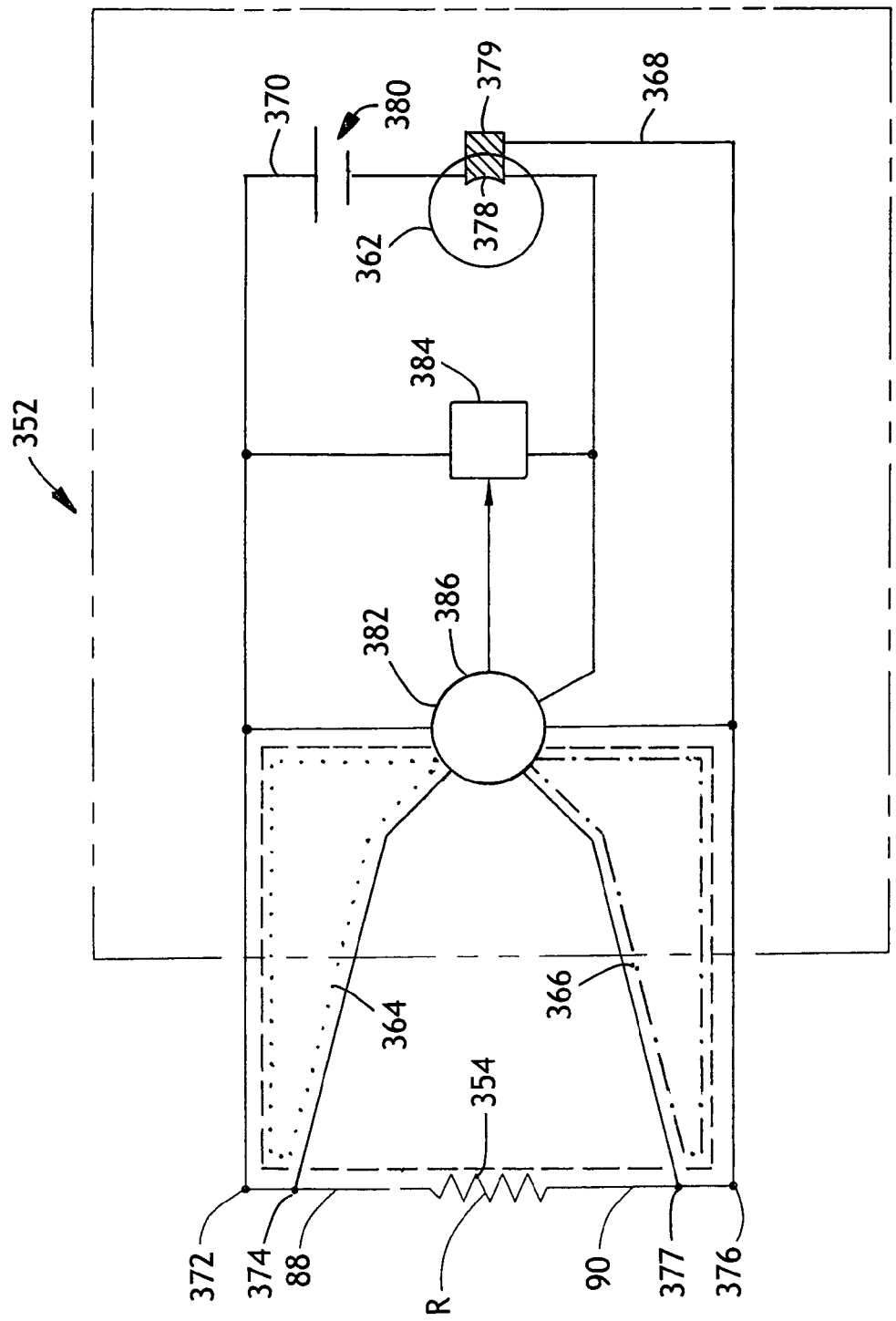
FIG. 24 is a schematic illustration of a wetness circuit, continuity monitoring circuits, attachment monitoring circuit, and power management circuit of the wetness monitoring system of FIG. 22.

Referring to FIG. 24, the monitor 352 includes a current source 380, a microprocessor 382, and an indicator 384. In the illustrated embodiment, a measuring device 386 is integral with the microprocessor 382. When the attachment legs are pivoted shut via the hinge 362, the fifth contact 378 is brought into electrical connection with the sixth contact 379 thereby completing the integrally activated and deactivated power circuit 370 and allowing the current to flow from the battery 380 to the various circuits 354, 364, 366, and 368. Also when the fifth contact 378 is brought into electrical connection with the sixth contact 379 the attachment monitoring circuit 368 is completed and the microprocessor 382 may be programmed to activate the indicator 384 to provide a notification to the wearer and/or care giver that the monitor 352 is securely attached to the absorbent article.

When the first contact 372 and the second contact 374 penetrate the liner 42 and contact the first conductor 88, the first continuity monitoring circuit 364 is completed. When the third contact 376 and the fourth contact 377 penetrate the liner 42 and contact the second conductor 90, the second continuity monitoring circuit 366 is completed. The wetness monitoring circuit 354 is completed when the first contact 372 electrically connects with the first conductor 88 and the third contact 376 electrically connects with the second conductor 90.

In various embodiments, the microprocessor 382 may be programmed to activate the indicator 384 or any other additional indicators to provide one or more indications when the wetness circuit 354 is complete, when the first continuity circuit 364 is complete, when the second continuity circuit 366 is complete, when the attachment circuit 368 is complete, or combinations thereof. When activated, the indicator 384 or indicators may be any suitable devices for providing notification of wetness, continuity, attachment, or combinations thereof, to the wearer and/or caregiver.

In various embodiments, the microprocessor may be programmed to activate the indicators to provide different indications when different circuits are completed and/or opened such that wearers and/or caregivers can determine what indication is being provided. For example, in some embodiments, the microprocessor may be programmed to activate an indicator to provide a first notification, such as a short "beep," when the continuity circuits are complete and may be programmed to activate an indicator to provide a second notification, such as a prolonged "alarm," when the wetness circuit detects an insult. In some embodiments, the microprocessor may be programmed to activate more than one indicator to provide different indications. For example, in some embodiments, the microprocessor may be programmed to activate a first indicator to provide a first notification, such as illuminating a light, when the continuity circuits are complete and may be programmed to activate a second indicator to provide a second notification, such as a vibration, when the microprocessor detects an insult in the wetness circuit.

While the invention has been described in detail with respect to specific embodiments thereof, it will be appreciated that those skilled in the art, upon attaining understanding of the foregoing, will readily appreciate alterations to, variations of, and equivalents to these embodiments. Accordingly, the scope of the present invention should be assessed as that of the appended claims and any equivalents thereto.

What is claimed is:

1. A monitor for use with an absorbent article having a wetness sensor, the monitor comprising, a microprocessor and a current source; wherein the microprocessor forms part of a first wetness monitoring circuit, part of a second wetness monitoring circuit, and part of a continuity monitoring circuit; wherein the microprocessor includes programming instructions to activate an indicator when both the first continuity monitoring circuit and the second continuity monitoring circuit are complete; the monitor further comprising a first contact, a second contact, a third contact and a fourth contact, wherein the first continuity monitoring circuit includes the first contact and the second contact, the first contact and the second contact being adapted to electrically connect the microprocessor with a first conductor associated with the absorbent article, wherein the first conductor forms part of the wetness sensor, and wherein the second continuity monitoring circuit includes the third contact and the fourth contact, the third contact and the fourth contact being adapted to electrically connect the microprocessor with a second conductor associated with the absorbent article, wherein the second conductor forms part of the wetness sensor.

2. The monitor of claim 1 wherein the wetness monitoring circuit includes at least one of the first contact or the second contact and includes at least one of the third contact or the fourth contact.

3. The monitor of claim 1 wherein the first, second, third and fourth contacts are adapted to physically penetrate through a bodyside liner or an outer cover of the absorbent article to electrically connect with the first and second conductors.

4. The monitor of claim 1 wherein the first, second, third and fourth contacts are adapted to snap onto the absorbent article to electrically connect with the first and second conductors.

5. The monitor of claim 1 wherein the microprocessor further forms part of an attachment monitoring circuit and wherein the microprocessor is adapted to provide an indication when the attachment monitoring circuit is complete.

6. The monitor of claim 5 wherein the monitor defines an open condition and a closed condition and the monitor includes a hinge and a housing, wherein the attachment monitoring circuit includes a first contact associated with the hinge and a second contact associated with the housing, the first contact being electrically connected with the second contact when the monitor is in the closed condition and the first contact being electrically disconnected with the second contact when the monitor is in the open condition.

7. A wetness monitoring kit, comprising,
the monitor of claim 1 and
an absorbent article having a wetness sensor, wherein the monitor and the article are adapted to physically connect together and the monitor and the wetness sensor are adapted to electrically connect together.

8. The wetness monitoring kit of claim 7 wherein
the wetness sensor of the absorbent article comprises a first conductor and a second conductor extending generally in a longitudinal direction and spaced apart in a lateral direction by a distance, D, and
the monitor further comprises a first contact, a second contact, a third contact and a fourth contact,
the first contact and the second contact being generally aligned in the longitudinal direction,
the third contact and the fourth contact being generally aligned in the longitudinal direction, and
the first contact and the second contact being spaced apart from the third contact and the fourth contact by a distance of about D as measured in the lateral direction.

9. The wetness monitoring kit of claim 8 further comprising instructions directing a wearer or caregiver to attach the monitor to the absorbent article such that the first contact and the second contact electrically connect with the first conductor and the third contact and the fourth contact electrically connect with the second conductor, the instructions further directing a wearer or caregiver to receive a notification when the monitor has continuity with the sensor, the instructions further directing the wearer or caregiver to reposition the monitor if no notification is received.

10. The wetness monitoring kit of claim 8, further comprising instructions directing a wearer or caregiver to attach the monitor to the absorbent article such that the first contact and the second contact electrically connect with the first conductor and the third contact and the fourth contact electrically connect with the second conductor, the instructions further directing a wearer or caregiver to receive a notification that the monitor has continuity with the sensor, the instructions further directing the wearer or caregiver to reposition the monitor if a notification is received indicating that continuity is broken.

11. A method of providing a system for monitoring an absorbent article with a wetness sensor comprising a first conductor and a second conductor, the method comprising,
providing a monitor having a first contact, a second contact, a microprocessor, and a current source, wherein the first contact is adapted to electrically connect with the first conductor of the wetness sensor, the second contact is adapted to electrically connect with the second conductor of the wetness sensor,
electrically connecting the first contact and the second contact with the microprocessor to form part of a monitoring circuit,
programming the microprocessor to measure an electrical property of the monitoring circuit,
programming the microprocessor to provide a first indication when the electrical property is above a first value,
programming the microprocessor to provide a second indication when the electrical property is below the first value and above a second value, and
programming the microprocessor to provide a third indication when the electrical property is below the second value.

12. The method of claim 11 wherein the first value is about 10 MΩ and the second value is about 1 MΩ.

13. The method of claim 12 wherein the first indication provides notification that the monitor is not electrically connected with the wetness sensor of the absorbent article, the second indication provides notification that the monitor is electrically connected with the wetness sensor, and the third indication provides notification that the absorbent article is wet.

14. A method of providing a monitor for use with a wetness sensor in an absorbent article, wherein the wetness sensor comprises a first conductor and a second conductor, the method comprising,
providing a monitor housing having a microprocessor associated therewith,
positioning a first contact and a second contact on the monitor housing to align with the first conductor of the wetness sensor,
positioning a third contact and a fourth contact on the monitor housing to align with the second conductor of the wetness sensor,
electrically connecting the first contact and the second contact with the microprocessor to define part of a first continuity monitoring circuit,
electrically connecting the third contact and the fourth contact with the microprocessor to define part of a second continuity monitoring circuit,
electrically connecting at least one of the first or second contacts and at least one of the third or fourth contacts with the microprocessor to define part of a wetness monitoring circuit,
programming the microprocessor to measure an electrical property of the first continuity monitoring circuit,
programming the microprocessor to measure an electrical property of the second continuity monitoring circuit, programming the microprocessor to provide a first indication when both the first continuity monitoring circuit and second continuity monitoring circuit are complete,
programming the microprocessor to measure an electrical property of the wetness monitoring circuit, and
programming the microprocessor to provide a second indication when an insult is detected in the wetness monitoring circuit.

15. The method of claim 14 wherein the monitor housing includes a pair of attachment legs pivotally attached by a hinge to a main housing and wherein the hinge includes a fifth contact and one of the attachment legs or the main housing includes a sixth contact, the method further comprising,
electrically connecting the fifth contact and the sixth contact with the microprocessor to define an attachment monitoring circuit,
programming the microprocessor to measure an electrical property of the attachment monitoring circuit, and
programming the microprocessor to provide a third indication when the fifth contact electrically connects with the sixth contact to complete the attachment monitoring circuit.

16. The method of claim 14 further comprising,
programming the microprocessor to provide a fourth indication when at least one of the first continuity monitoring circuit or the second continuity monitoring circuits are opened after both circuits have been closed.

17. The method of claim 14 wherein the monitor housing includes a pair of attachment legs pivotally attached by a hinge to a main housing, the method further comprising,
positioning at least one of the first, second, third or fourth contacts on the attachment legs,
positioning a receptacle on the main housing to align with the at least one contact when the monitor is in a closed condition,
electrically connecting the at least one contact and the receptacle with the microprocessor to define an attachment monitoring circuit, and
programming the microprocessor to provide a third indication when the at least one contact electrically connects with the receptacle to complete the attachment monitoring circuit.

* * * * *